(12) United States Patent
Gaire et al.

(10) Patent No.: US 11,315,240 B2
(45) Date of Patent: Apr. 26, 2022

(54) SYSTEM AND METHOD OF TUMOR CLASSIFICATION

(71) Applicant: HOFFMANN-LA ROCHE INC., Little Falls, NJ (US)

(72) Inventors: Fabien Gaire, Starnberg (DE); Eldad Klaiman, Starnberg (DE); Konstanty Korski, Poznan (PL)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 381 days.

(21) Appl. No.: 16/301,945

(22) PCT Filed: May 18, 2017

(86) PCT No.: PCT/EP2017/062037
§ 371 (c)(1),
(2) Date: Nov. 15, 2018

(87) PCT Pub. No.: WO2017/198790
PCT Pub. Date: Nov. 23, 2017

(65) Prior Publication Data
US 2019/0287240 A1   Sep. 19, 2019

(30) Foreign Application Priority Data

May 18, 2016 (EP) .................................. 16170224
Nov. 29, 2016 (EP) .................................. 16201272

(51) Int. Cl.
*G06T 7/00* (2017.01)
*G16H 30/40* (2018.01)
*A61B 5/107* (2006.01)

(52) U.S. Cl.
CPC .......... *G06T 7/0012* (2013.01); *G16H 30/40* (2018.01); *A61B 5/1075* (2013.01); *G06T 2207/30096* (2013.01)

(58) Field of Classification Search
None
See application file for complete search history.

(56) References Cited

U.S. PATENT DOCUMENTS

| 2015/0133321 | A1* | 5/2015 | Bhaumik | G06T 7/0012 |
| | | | | 506/9 |
| 2016/0123964 | A1* | 5/2016 | Tumeh | C07K 16/2818 |
| | | | | 424/133.1 |

(Continued)

FOREIGN PATENT DOCUMENTS

WO   WO-2015189264 A1 * 12/2015 ........... G06T 7/0012

OTHER PUBLICATIONS

International Preliminary Report and Written Opinion for corresponding PCT Application No. PCT/EP2017/062037 dated Nov. 29, 2018.

(Continued)

*Primary Examiner* — Benny Q Tieu
*Assistant Examiner* — Pawan Dhingra
(74) *Attorney, Agent, or Firm* — Harness, Dickey & Pierce, P.L.C.

(57) ABSTRACT

At least one embodiment relates to an image analysis system for tumor classification. The system is configured for receiving at least one digital image of a tissue sample; analyzing the at least one received image for identifying immune cells and tumor cells in the at least one received image; for each of the identified tumor cells, determining the distance of the tumor cell to the nearest immune cell; computing a proximity measure as a function of the determined distances; in dependence on the proximity measure, classifying the identified tumor cells into tumor cells of an inflammatory tumor or as tumor cells of a non-inflammatory tumor; and storing the classification result on a storage medium and/or displaying the classification result on a display device.

20 Claims, 11 Drawing Sheets

(56) References Cited

U.S. PATENT DOCUMENTS

2017/0076442 A1* 3/2017 Schoenmeyer ........ G16H 30/40
2019/0287249 A1* 9/2019 Gaire ................. G06K 9/00147

OTHER PUBLICATIONS

International Search Report PCT/ISA/210 for International Application No. PCT/EP2017/062037 dated Sep. 27, 2017.
Written Opinion of the International Searching Authority PCT/ISA/237 for International Application No. PCT/EP2017/062037 dated Sep. 27, 2017.
Juliane M. Krüger et al. "Combat or surveillance? Evaluation of the heterogeneous inflammatory breast cancer microenvironment", The Journal of Pathology, vol. 229, No. 4, Feb. 15, 2014, pp. 569-578.

* cited by examiner

CRC Tumor Samples with Genetic Status: MSS

Tumor Samples with Genetic Status: MSS

Tumor Samples with Genetic Status: MSS

Distances: [KI67+ ↔ [CD3+/CD8+;CD3+/CD8+;KI67+]

Two cases with similar T-cell densities

Case A

MSS

4% of the tumor cells are
in close contact to T-cell

KI67 tumor cell

CD8 T-cell

Case B

MSI

21% of the tumor cells are
in close contact to T-cell

KI67 tumor cell

CD8 T-cell

SYSTEM AND METHOD OF TUMOR CLASSIFICATION

CROSS-REFERENCE TO RELATED APPLICATIONS

This application is a national phase under 35 U.S.C. § 371 of PCT International Application No. PCT/EP2017/062037 which has an International filing date of May 18, 2017, which claims priority to European Application No. 16201272.8, filed Nov. 29, 2016, and European Application No. 16170224.6, filed May 18, 2016, the entire contents of each of which are hereby incorporated by reference.

FIELD OF THE INVENTION

The invention relates to the field of image analysis, and more particularly to the field of image-based tumor classification.

BACKGROUND AND RELATED ART

Microsatellite instability (MSI) is the condition of genetic hypermutability that results from impaired DNA mismatch repair (MMR). The presence of MSI represents phenotypic evidence that MMR is not functioning normally and thus is an indicator of the genetic state of a cell considered as a potential tumor cell.

Microsatellite instability is known to be associated with colon cancer, gastric cancer, endometrium cancer, ovarian cancer, hepatobiliary tract cancer, urinary tract cancer, brain cancer, and skin cancers. MSI is most prevalent as the cause of colon cancers. Each year, there are over 500,000 colon cancer cases worldwide. Based on findings from over 7,000 patients stratified for MSI-High (MSI-H), MSI-Low (MSI-L), or Microsatellite Stable (MSS) colon cancers, those with MSI-H had a more positive prognosis by 15% compared to MSI-L or MSS tumors.

MSI is a good marker for determining a prognosis for cancer treatments. Additional approaches which are based on genetic information of a tumor exist. For example, extensive research is ongoing to decipher the underlying genetic patterns of tumor tissue cells with the hope to improve early cancer diagnosis and treatment. The recent progress in next generation sequencing technologies has revolutionized the field of cancer genomics. However, one caveat of these studies remains the large amount of genetic variations identified and their interpretation.

SUMMARY

It is an objective of the present invention to provide for an improved method and image analysis system for classifying tumor cells as specified in the independent claims. Embodiments of the invention are given in the dependent claims. Embodiments of the present invention can be freely combined with each other if they are not mutually exclusive.

In one aspect, the invention relates to an image analysis method for tumor classification. The method comprises:
- receiving, by an image analysis system, at least one digital image of a tissue sample;
- analyzing, by the image analysis system, the at least one received image for identifying immune cells and tumor cells in the at least one received image;
- for each of the identified tumor cells, determining, by the image analysis system, the distance of said tumor cell to the nearest immune cell;
- computing, by the image analysis system, a proximity measure as a function of the determined distances;
- in dependence on the proximity measure, classifying, by the image analysis system, the identified tumor cells into tumor cells of an inflammatory tumor or as tumor cells of a non-inflammatory tumor; and
- storing, by the image analysis system, the classification result on a storage medium and/or displaying the classification result on a display device.

Said approach for classifying the identified tumor cells into cells of an inflammatory vs. non-inflammatory tumor may be advantageous for multiple reasons:

The distance of immune cells and tumor cells appears to more accurately reflect cellular processes related to the immune response of an organism against a tumor than, for example, the MSS/MSI status. Thus, the proximity measure appear to more accurately reflect the inflammatory status of a tumor (an inflammation is—very generally speaking—the body's immune system's response to a stimulus) than a genetic approach. It has been observed that at least in some cases inflammatory versus non-inflammatory tumor were correctly distinguished based on the proximity measure which were not correctly distinguished based on their MSS/MSI status.

The high mutational load in MSI tumors creates many tumor-specific neoantigens, typically 10-50 times that of MSS tumors. Some of these neoantigens will be processed, presented on MHC, and recognized as foreign by T cells. The high neoantigen burden might be one explanation for the high level of tumor-infiltrating lymphocytes ("inflammatory tumor state") in MSI tumors. MSI tumors have a better prognosis than MSS tumors and respond better to several classes of drugs which boost or modulate the immune response. By determining a proximity measure based on the individual distances of tumor cells and immune cells, a more accurate classification of inflammatory vs. non-inflammatory tumors can be made and/or a more accurate prognosis and treatment recommendation (whether or not to prescribe a drug that boosts or modulates the immune response) can be given.

According to a further beneficial aspect, the proximity measure can quickly be computed from a digital image of a tumor tissue sample having been stained with an immunofluorescence assay. Thus, an additional time consuming and expensive (and-as it appears-less accurate) MSS/MSI status analysis of tumor cells may be avoided.

In a further beneficial aspect (compared to e.g. to various immune score computations), and increased accuracy of tumor classification and prognosis may be achieved, because distances between individual immune cells and tumor cells are determined. Instead of roughly determining the outline of a tumor region and then determining whether an immune cell is contained in said tumor region or not, embodiments of the invention use individual immune cell-tumor cell distances as a basis for computing a proximity measure from all said determined distances. This proximity measure is a more accurate indication of whether immune cells and tumor cells are located sufficiently close to each other to allow for an effective immune response against the tumor cells. In other words, the proximity measure for example indicates whether a sufficiently large number of immune-promoting immune cells such as cytotoxic T cells, B cells, memory cells, T-helper cells and/or macrophages are within an "immunologically effective distance" from the tumor cells.

An "immunologically effective distance" as used herein is a distance between an immune cell and its nearest tumor cell which is sufficiently small to allow for the killing of said tumor cell by said immune cell. The killing of the tumor cell may be performed directly or indirectly and may be performed by different pathways which may depend on the type of immune cell. For example, the killing of the tumor cell may be achieved via direct cell-cell interaction between the immune cell and the tumor cell, via a direct or signal-molecule based interaction of said immune cell with a further immune cell in the proximity of the tumor cell whereby the further immune cells kills or triggers the apoptosis of the tumor cell, or by triggering the apoptosis of the tumor cell (e.g. via direct cell-cell interaction or via signal molecules secreted by the immune cell).

In a further beneficial aspect, the distance information may not only be used as an input for accurately classifying tumor as an inflammatory versus a non-inflammatory tumor, the distance information may also be used for generating a graphical output that may allow a pathologist to easily and accurately identify the location and distribution of inflammatory regions within a tumor tissue.

In a further beneficial aspect, once the individual immune cells and tumor cells have been identified, the distance computation for individual pairs of neighboring tumor cells and in immune cells may be performed very quickly and efficiently. As the computed distances on numerical values, also the proximity measure computation as a function of a plurality of numerical values may be performed quickly and with comparatively low computational effort even in case in the depicted tissue sample comprises many thousand cells.

In a further aspect, the invention relates to an image analysis method for tumor classification. The method comprises:
- receiving, by an image analysis system, at least one digital image of a tissue sample;
- analyzing, by the image analysis system, the at least one received image for identifying tumor cells in the at least one received image;
- analyzing, by the image analysis system, the identified tumor cells for identifying tumor regions, wherein a tumor region is a tissue region whose majority of cells consist of tumor cells;
- analyzing, by the image analysis system, the at least one received image for identifying immune cells lying within one of the identified tumor regions or lying within a boundary region around one of the tumor regions, the width of the boundary being smaller than 200 µm;
- for each of the identified immune cells, determining, by the image analysis system, the distance of said immune cell to the nearest tumor cell;
- computing, by the image analysis system, a proximity measure as a function of the determined distances;
- in dependence on the proximity measure, classifying, by the image analysis system, the identified tumor cells into tumor cells of an inflammatory tumor or as tumor cells of a non-inflammatory tumor; and
- storing, by the image analysis system, the classification result on a storage medium and/or displaying the classification result on a display device.

Thus, according to said alternative approach, at first the tumor cells and corresponding tumor regions are identified in the digital image. Then, immune cells in said tumor regions or within close spatial proximity to said tumor regions are identified and the immune cell-tumor cell distances are identified. In this scenario, the distances may be computed starting from the individual identified immune cells ("for each identified immune cell") or may be computed starting from the individual identified tumor cells (for each identified tumor cell"). For example, gray scale and color segmentation techniques, edge detection, voting and radial symmetry based image analysis techniques can be used for identifying and/or classifying cells and for identifying regions consisting of or mainly comprising similarly colored or shaped cells having been identified as tumor cells. Moreover, various machine learning techniques with supervised learning methods such as SVM (Support vector Machines), DNN (Deep Neural Networks), Random Forest, etc. can be used to classify cells into types and/or to identify tumor regions, non-tumor tissue regions and glass regions on a slide. Limiting the distance determination on the tumor and its boundary may ensure that in case a whole tissue slide comprises only a small tumor region and the majority of immune cells is located far away from the tumor, the effect of said distant immune cells (which may be present in said far-away regions irrespective of whether the tumor is inflammatory or not) does not modify the proximity measure.

According to embodiments, the image analysis method further comprises analyzing the received digital image for determining a tumor cell density of the identified tumor cells. The classification of the identified tumor cells into tumor cells of an inflammatory tumor or as tumor cells of a non-inflammatory tumor comprises inputting the proximity measure and the tumor cell density into a classifier configured to perform the classification.

According to embodiments, the image analysis method further comprises analyzing the received digital image for determining an immune cell density of the identified immune cells or of a particular type of immune cells (e.g. T-cells, B-cells, macrophages, etc.). The classification of the identified tumor cells into tumor cells of an inflammatory tumor or as tumor cells of a non-inflammatory tumor comprises inputting the proximity measure and the immune cell density into a classifier configured to perform the classification.

According to embodiments, the classification of the identified tumor cells into tumor cells of an inflammatory tumor or as tumor cells of a non-inflammatory tumor comprises inputting the proximity measure, the tumor cell density and the immune cell density into a classifier configured to perform the classification.

According to some embodiments, the determination of the tumor cell density comprises determining the tumor cell density for each tumor cell individually, e.g. by determining the tumor cell density in a predefined area centered around said tumor cell. In this case, each of the determined tumor cell density values can be fed as input into the classifier. Alternatively, an average value is computed from the individual density values and is input as a single value into the classifier. Likewise, the determination of the immune cell density comprises determining the immune cell density for each immune cell individually, e.g. by determining the immune cell density in a predefined area centered around said immune cell. In this case, each of the determined immune cell density values can be fed as input into the classifier. Alternatively, an average value is computed from the individual density values and is input as a single value into the classifier.

Using cell density information as an additional input parameter of the classifier may be advantageous as the accuracy of the classification may significantly be increased.

According to embodiments, the displaying of the classification result comprises representing all identified tumor cells as first pixel blobs having a first color and representing all identified immune cells whose distance to its nearest tumor cells is below a threshold as second pixel blobs having a second color. Then, the image analysis system displays the second pixel blobs as an overlay of the first pixel blobs.

For example, the tissue sample may be a biopsy sample of colorectal cancer, the identified immune cells may be cytotoxic T cells and the distance threshold may be 35 µm. All cells having been identified as tumor cells may be colorized with blue color and may correspond to a first image layer. All cells having been identified as immune cells whose distance to its nearest tumor cell is below 35 µm are colorized with orange color and may correspond to a second image layer. The second image layer is superimposed on the first image layer with the consequence that the orange "tumor affine" immune cells cover and hide at least some of the tumor cells. In this case, orange regions in the tumor tissue indicate inflammatory regions. If the tissue section represented in the generated overlay-image comprises only few orange regions, the immune response is predicted to be only weak or is predicted not to significantly affect tumor development. The patient in this case is predicted not profit from the application of drugs boosting or modulating the immune response because the immune cells are too far away from the tumor cells as to be able to kill them. Thus, a user of pathologist can immediately and easily derive from such an overlay image if a particular tumor tissue is inflammatory or not and/or whether the treatment of the patient with substances known to boost or modulate an immune reaction will be effective in treating this tumor or not.

According to embodiments, the tissue sample is a whole slide tissue sample and the digital image is a whole slide image. Typically, such whole slide tissue samples comprise several thousand or even 10,000s of cells. Thus, the proximity measure may be a function of the distances of many thousand neighboring immune cell-tumor cell pairs.

According to embodiments, the identification of the tumor cells comprises identifying proliferating non-lymphoid cells and using said identified cells as the tumor cells.

For example, proliferating cells may be identified by using generic proliferation markers such as fluorescent stained antibodies binding to the KI67 protein or to the PCNA protein. Non-lymphoid cells are identified, for example, as cells which do not express typical immune cell markers such as CD3. Thus, any cell having the expression profile KI67+/CD3− is identified as a proliferating non-lymphoid cells and thus as a tumor cell. This approach may be beneficial as it provides a very generic way of identifying tumor cells that is applicable for many different types of tumors and for many different types of tissues.

In addition, or alternatively, the identification of the tumor cells comprises identifying cells expressing a (specific) set of one or more tumor-specific biomarkers and using said identified cells as the tumor cells.

For example, a cytokeratin profile (data indicating whether a particular set of cytokeratins is expressed in a cell or not) of the cells in the tissue sample is determined, e.g. by using fluorescence stains selectively staining the respective cytokeratins. The obtained cytokeratin profile is then compared by the image analysis system against known cytokeratin profiles of various tissues such as liver, lung, colon and so on. In case the cytokeratin profile of a cell in the tissue sample depicted in the image differs from the typical cytokeratin profile of the tissue from which the tissue sample was taken, the cells having this "deviant/untypical" cytokeratin profile are automatically or semi-automatically identified as tumor cells.

Cytokeratins are proteins of keratin-containing intermediate filaments found in the intracytoplasmic cytoskeleton of epithelial tissue. For example, basic cytokeratins CK1, CK2, CK3, CK4, CK5, CK6, CK7, CK8 and acidic cytokeratins CK9, CK10, CK12, CK13, CK14, CK16, CK17, CK18, CK19, and CK20 are known. Expression of these cytokeratins is frequently organ or tissue specific. Therefore, cytokeratin expression profiles can be used by anatomic pathologists to detect the presence and/or cell of origin of various tumors.

Depending on the type of tissue of the tissue sample and/or the type of the tumor suspected to be present in a patient, the presence (sufficiently high expression level) of other tumor-specific biomarkers may be determined, e.g. the presence of the Her2 protein fur breast cancer.

According to embodiments, the identification of the immune cells comprises or consists of identifying cytotoxic T-cells and using the identified cytotoxic T-cells as the identified immune cells. For example, the CD8 protein that is specifically expressed in cytotoxic T-cells is used as a biomarker. A stain that selectively binds to the CD8 protein in the tissue sample is used and an image whose pixel intensity values are indicative of the presence of the CD8 protein is taken from the stained tissue sample. An image analysis operation is performed on the CD8 biomarker related staining and intensity signal, e.g. a threshold-based blob detection operation, and the corresponding pixel blob is identified as CD8+ cell and thus as a cytotoxic T-cell.

According to other embodiments, CD8+ and CD3+ cells (i.e., cells expressing both the CD8 protein and the CD3 protein) are identified as cytotoxic T-cells. The CD3 protein is a protein expressed on many different immune cells and is used as a further biomarker that helps to ensure that a particular blob is really an immune cell and not, for example, an artifact created by an unspecific staining reaction of the antibody used for staining the CD8 protein.

In addition, or alternatively, the identification of the immune cells comprises or consists of identifying T-helper-cells and using the identified T-helper-cells as the identified immune cells. For example, CD4 expressing cells ("CD4+ cells") are identified as T-helper cells. According to other examples, cells expressing both the CD4 and the CD3 protein ("CD4+/CD3+ cells") are identified as T-helper-cells. Again, CD3 protein expression was used as a further indicator to make sure a blob is really an immune cell, not a blob of an unspecific stain. Instead of or in addition to the CD4 marker, the T-bet marker may likewise be used for identifying T-helper cells.

In addition, or alternatively, the identification of the immune cells comprises or consists of identifying memory cells and using the identified memory cells as the identified immune cells. For example, CD45RO expressing cells ("CD45RO+ cells") are identified as memory cells.

In addition, or alternatively, the identification of the immune cells comprises or consists of identifying B-cells and using the identified B cells as the identified immune cells. For example, CD20 expressing cells ("CD20+ cells") are identified as B-cells.

In addition, or alternatively, the identification of the immune cells comprises or consists of identifying activated T-cells and using the identified activated T-cells as the identified immune cells. For example, CD137 expressing cells ("CD137+ cells") are identified as activated T-cells.

In addition, or alternatively, the identification of the immune cells comprises identifying PD1+ immune cells and using the identified PD1+ immune cells as the identified immune cells. In addition, the identification of the tumor cells comprises identifying PDL1+ tumor cells and using the identified PDL1+ tumor cells as the identified tumor cells. A PDL1+ tumor cell is a tumor cell that expresses the PDL1 protein. For example, as mentioned before, a tumor cell can be identified e.g. as a cell expressing the KI67 protein and/or expressing the PCNA protein and not expressing a CD3 protein. Thus, a PDL1+ tumor cell would be a cell having the expression profile PDL1+/KI67+/CD3−. Alternatively, any other biomarker indicating that a cell is a tumor cell (e.g. panCK+ or a particular cytokine profile that deviates from the profile of the surrounding tissue) can be used for identifying tumor cells.

A cell that "expresses" a biomarker BM ("BM+ cell") as used herein refers to a cell expressing said biomarker at least in a minimum amount. For example, the question if said minimum amount is generated can be determined by comparing an intensity value on a respective digital image with an intensity threshold value. Said threshold value may be specific for the biomarker or stain used. Depending on the type of biomarker examined, a cell that "expresses" a biomarker can also be a cell that expresses a greater amount of said biomarker than a "typical" cell of said cell type or than another reference cell type. In this case, the label "BM+ cell" refers to a cell that over-expresses the biomarker BM (relative to a reference expression level).

Programmed death-ligand 1 (PDL1) is a 40 kDa type 1 transmembrane protein that plays a major role in suppressing the immune system during particular events such as pregnancy, tissue allografts, autoimmune disease and other disease states such as hepatitis. Normally the immune system reacts to foreign antigens by triggering proliferation of antigen-specific CD8+ T cells.

Programmed cell death protein 1 (PD1) is a cell surface receptor that belongs to the immunoglobulin superfamily and is expressed on T cells and pro-B cells. PD1 binds two ligands, PDL1 and PD-L2. PD1 is an immune checkpoint and plays an important role in down regulating the immune system by preventing the activation of T-cells. PD1 is expressed on the surface of activated T cells, B cells, and macrophages.

The formation of PD1/PDL1 ligand complex transmits an inhibitory signal on the immune response. It appears that some cancers upregulate PDL1 expression, thereby managing to evade the host immune system. High expression of PDL1 by tumor cells has been observed to be associated with increased tumor aggressiveness and an increased risk of death.

By computing the proximity measure in by using the above mentioned PDL1/PD1 biomarkers, it is possible to determine if the immune cells lying within an immunologically effective distance from the tumor cells express PD1 receptor protein or not and to determine if the tumor cells (over)express the PDL1 protein.

In addition, or alternatively, the identification of the immune cells comprises or consists of identifying macrophages and using the identified macrophages as the identified immune cells. For example, cells expressing both the CD163 and the CD68 protein ("CD163+/CD68+ cells") are identified as macrophages. Instead of or in addition to the CD163 marker, the CSF1R marker may likewise be used for identifying macrophages.

It has been observed that automated full slide analysis of a cohort of slides stained with an immunofluorescence assay targeting the biomarkers CD3, CD4, CD8 and KI67 reveals that metrics of CD3+/CD8+ and CD3+/CD4+ immune cell distribution and proximity to KI67+ proliferating non-lymphoid cells (CD3−/KI67+) in the tumor area can serve as a strong indicator for immune response in the tumor area. By computing a proximity score that is based on individual tumor cell-immune cell distances, a particularly accurate tumor classification method is provided that is more accurate than state of the art MSS/MSI state based or immunoscore based classification schemes. Moreover, the proposed computation of a cell distance based proximity score and the use of the score for tumor classification has been observed in colorectal cancers to have a higher prognostic value than the AJCC/UICC TNM-classification.

Cytotoxic T-cells, memory cells, T-helper cells and macrophages are immune cells which are responsible or are able to initiate and/or boost an immune response. To the contrary, regulatory T-cells are often involved in the downregulation of the immune response. Thus, by selectively identifying those immune cells having a positive or stimulatory effect on the immune response, and by selectively identifying the distances of said positively stimulating immune cells, an even higher accuracy of the proximity score derived from said distances can be achieved: the presence of regulatory T-cells potentially having a negative impact on the immune response are ignored, thereby preventing the computation of a proximity score that indicates that many immune cells are in close proximity to tumor cells in a situation when predominantly regulatory T-cells but not macrophages, cytotoxic T-cells and/or T-helper cells are in close proximity to individual tumor cells.

According to embodiments, the identification of the immune cells comprises or consists of identifying immune cell of one or more immune cell types that boost an immune reaction (e.g. macrophages, cytotoxic T-cells, memory cells, B cells, and T-helper cells) and ignoring ("filtering out") immune cells of an immune cell type that suppresses or downregulates an immune reaction (e.g. regulatory T-cells). Thus, the totality of identified immune cells used for computing the proximity measure may consist of immune cells of the same or of multiple different immune cell types. In this case, for computing the proximity measure as a function (e.g. a ratio or a histogram slope) of the distances, immune cell type specific functions (e.g. with immune cell type specific distance thresholds corresponding to immune cell type specific immunologically effective distances of said immune cell type) are used. For example, the immune cell ratios may be computed for each immune cell type individually and immune cell type specific ratios may be computed for immune cell type specific distance thresholds being identical to the immunologically effective distance of said immune cell type. Then, an average, e.g. the arithmetic mean of the immune cell type specific ratios may be computed as a final ratio and used as the proximity measure, for example. In case the immunologically effective distance of the different immune response boosting immune cell types is identical or very similar, the same function, e.g. the same distance threshold for ratio computation may be used for multiple or all immune cell types considered.

Computing a single proximity measure from multiple different immune cell types (using the same or immune cell type specific function of the tumor cell-immune cell distances) may be advantageous as a better and more complete data basis of the spatial relationship between relevant immune response promoting immune cells and their potential targets, the tumor cells, is provided and a more accurate classification into inflammatory and non-inflammatory tumor cells may be provided.

In addition, or alternatively, multiple individual proximity measures may be computed for multiple respective immune cell types and/or tumor cell types, e.g. for determining if a tumor of a tissue sample is a PDL1+ tumor and if a sufficient portion of the tumor cells is within an immunologically effective distance of a PD1+ immune cell. Said additional proximity measures may allow for a further sub-classification of the tumor and for a better prediction of the treatment schema.

According to embodiments, the identification of the immune cells comprises identifying regulatory T-cells and identifying immune cells of at least one type of immune cells that boosts the immune response and selectively using the identified immune cells that boost the immune response but not the identified regulatory T-cells as the identified immune cells. For example, cells expressing the FoxP3 protein ("FoxP3+ cells") are identified as regulatory T-cells and are ignored when the tumor cell-immune cell distances are determined. According to other embodiments, FoxP3+/CD3+ cells are identified as regulatory T-cells, whereby the expression of the CD3 biomarker is used as a further indicator to make sure a blob is really an immune cell, not a blob of an unspecific stain.

According to embodiments, the proximity measure is determined multiple times as described herein for embodiments of the invention, thereby respectively analyzing different digital images whose pixel intensities represent different biomarkers, the different biomarkers being indicative of immune cells of different types (e.g.: CD8 for cytotoxic T-cells, FoxP3 for regulatory T-cells, CD163 or CSF1 R for macrophages, CD20 for B-cells, CD137 for activated T-cells, PD1 for some tub-types of T- and pro-B cells) and/or being indicative of tumor cells of different types (e.g. PDL1+/PDL1− tumor cells. Each of said multiple proximity measures may be used as a predictor of tumor cell class and/or prognosis and/or of a suitable treatment scheme.

Computing the proximity measure multiple times for different types of immune cell types and/or cancer cell types may allow to more accurately predict which ones of different classes of immune response modulating drugs will be effective in treating the tumor and which ones will not. By combining information contained in the spatial proximity of different immune cell and tumor cell types, the accuracy of classifying the tumor into inflammatory or non-inflammatory tumors may be increased and a classification into further sub-classes of tumors (e.g. PDL1+ or PDL1− tumors) may be enabled. In addition, the accuracy of a prediction if a particular drug class will be effective in treating the tumor may increase.

When computing multiple proximity measures for different immune cell sub-types and/or different tumor cell sub-types, also immune cells having an inhibitory effect on the immune system are taken into account. Although their presence within an immunologically effective distance from tumor cells may not indicate that the tumor is an inflammatory tumor, information on their spatial proximity to tumor cells may allow predicting whether applying a drug suppressing said inhibitory immune cell types may boost the immune response against the tumor.

According to embodiment, the image analysis system automatically outputs a prediction whether or not a particular class of drugs, will be effective in treating the cancer or not.

For example, one of said classes of drugs can be PD1 inhibitors. PD1 inhibitors activate the immune system to attack tumors and are used with varying success to treat some types of cancer by blocking or otherwise inhibiting the activity of the PD1 receptor. According to embodiment, the image analysis system is configured to predict that the PDL1 inhibitors will be effective only in case the proximity measure indicates that a sufficiently large fraction of PDL1+ tumor cells comprises at least one PD1+ immune cell within the predefined distance (immunologically effective distance). If the immune cells are not within an immunologically effective distance from the tumor cells or if the immune cells are located within said distance next a PDL1+ tumor cell but are not expressing PD1, the image analysis system is configured to predict that an anti-PDL1 drug will not to be effective in treating the tumor.

Likewise, other drug classes exist which boost or modulate an immune response and which specifically modulate the activity of individual immune cell types such as macrophages, T helper cells, B-cells, cytotoxic T-cells (T-cell engaging agents) and others. It may also be possible that said immune response modulating or boosting drugs are only effective in respect to specific tumor types. By automatically computing the proximity measure for multiple different immune cell types and/or tumor cell types, in a single step quantitative location information (cell-cell distance smaller than immunologically effective distance or not) as well as qualitative information on the cell classes is used as a basis for predicting whether or not a particular drug class will be effective in treating the tumor or not.

According to embodiments of the invention wherein the distances are determined for each of the identified tumor cells, the computation of the proximity measure as a function of the determined distances comprises:

identifying a first and a second sub-set of the identified tumor cells; the first sub-set ("tumor cells with a near immune cell") selectively comprising tumor cells whose nearest immune cell is less than a predefined distance away; the second sub-set ("tumor cell with far immune cells") selectively comprising tumor cells whose nearest immune cell is at least the predefined distance away from the tumor cell; for example, the predefined distance can be the "immunologically effective distance" of the identified immune cells;

computing a ratio of the number of tumor cells contained in the first subset and the number of tumor cells in the second sub-set; and using the ratio as the proximity measure, wherein the higher the ratio, the higher the probability that the classification result indicates that the identified tumor cells belong to the inflammatory tumor.

According to alternative embodiments of the invention wherein the distances are determined for each of the identified immune cells, the computation of the proximity measure as a function of the determined distances comprises:

identifying a first and a second sub-set of the identified immune cells, the first sub-set selectively comprising immune cells whose nearest tumor cell is less than a predefined distance away, the second sub-set selectively comprising immune cells whose nearest tumor cell is at least the predefined distance away from the tumor cell;

computing a ratio of the number of immune cells contained in the first subset and the number of immune cells in the second sub-set; and using the ratio as the proximity measure, wherein the higher the ratio, the higher the probability that the classification result indicates that the identified tumor cells belong to the inflammatory tumor.

According to embodiments, the predefined distance is the "immunologically effective distance" of the immune cell. The immunologically effective distance is a maximum distance within which the identified immune cell is able to directly or indirectly trigger the killing of or the performing of apoptosis by the tumor cell.

According to embodiments, the predefined distance is larger than 15 μm.

According to embodiments, the predefined distance is in a range of 20 μm to 50 μm, e.g. 35 μm.

For example, the tumor type may be colorectal cancer, the distance may be 35 μm. For other tumor types, the distance may slightly vary, but typically lies in the range of 20 μm to 50 μm.

According to embodiments the classification result indicates that the identified tumor cells belong to the inflammatory tumor in case the ratio exceeds a predefined percentage or threshold, typically 50%. Thus, according to one embodiment, the classification result indicates that the identified tumor cells belong to the inflammatory tumor in case the number of tumor cells contained in the first subset is larger than the number of tumor cells in the second sub-set (and thus, the fraction of the tumor cells in the first subset exceeds 50% of all tumor cells).

According to embodiments related to the determination of the distances for each of the tumor cells, the computation of the proximity measure as a function of the determined distances comprises:

generating a histogram of the distances of the tumor cells to their respective nearest one of the identified immune cells; the histogram comprises at least two distance bins; the histogram covers a distance range of 0 μm to at least 50 μm (typically up to 80 μm), each of the bins corresponding to a bar of the histogram, each of the bars indicating a count of the identified tumor cells having a distance to their nearest immune cell that falls into said bin;
  connecting the upper end of the first one of the bars with the upper end of the last one of the bars with a line; the line may be straight or curved; for example, the line may be a balance line; the first bar corresponds to the one of the bins covering the smallest distances; the last bar corresponds to the one of the bins covering the largest distances of the distance range;
  determining the slope of the line; for example, the first bar may be located at the left boundary of the histogram, the last bar may be located at the right boundary of the histogram, and the slope may be determined of the line connecting the left-side, first bar with the right-side last bar;
  using the slope as the proximity measure, wherein in case the slope indicates that the tumor cell count of the first bar is higher than the tumor cell count of the last bar (i.e., is negative if the first bar is plotted to on the left side of the histogram), the classification result is that the identified tumor cells belong to an inflammatory tumor.

According to embodiments related to the determination of the distances for each of the immune cells, the computation of the proximity measure as a function of the determined distances comprises:

generating a histogram of the distances of the immune cells to their respective nearest one of the identified tumor cells, the histogram comprising at least two distance bins, the histogram covering a distance range of 0 μm to at least 50 μm, each of the bins corresponding to a bar of the histogram, each of the bars indicating a count of the identified immune cells having a distance to their nearest tumor cell that falls into said bin;
  connecting the upper end of the first one of the bars with the upper end of the last one of the bars with a line, the first bar corresponding to the one of the bins covering the smallest distances, the last bar corresponding to the one of the bins covering the largest distances of the distance range;
  determining the slope of the line;
  using the slope as the proximity measure, wherein in case the slope indicates that the immune cell count of the first bar is higher than the immune cell count of the last bar, the classification result is that the identified tumor cells belong to an inflammatory tumor.

Computing a histogram slope as the proximity measure may have the advantage that the histogram that needs to be computed for determining the slope can be used as graphical output that visually represents the relative immune cell-tumor cell distribution in a tissue sample. The histogram may be output via a display device, thereby providing a user, e.g. a pathologist, with valuable information on the distance distribution of immune and tumor cells.

According to embodiments, the image analysis system outputs a signal selectively in case the classification result indicates that the identified tumor cells belong to an inflammatory tumor, wherein the signal is indicative of a treatment recommendation to use a substance that boosts or modulates an immune response as a drug for treating the tumor.

According to embodiments, the method comprises using the proximity measure in addition to or in replacement of an MSS-MSI status indicator for computing a prognosis of the responsiveness of the tumor to a substance that boosts or modulates an immune response.

According to embodiments, the identified tumor cells are colorectal cancer cells. However, the method and system according to embodiments of the invention are also applicable to other tumor types, e.g. breast cancer, pancreatic cancer, lung cancer, and the like.

According to embodiments, the identification of the immune cells comprises identifying immune cells of multiple different immune cell types by analyzing pixel intensity values in the at least one digital image, whereby the pixel intensities represent the presence of different immune cell type specific biomarkers, and using the totality of the identified immune cells of the multiple different immune cell types as the identified immune cells for computing the proximity measure.

According to embodiments, the tumor cells are identified as cells expressing at least a first tumor-type specific biomarker. The immune cells being identified as cells expressing at least a first immune cell type specific biomarker. The method further comprises:

analyzing the at least one received image or a further image of the tissue sample for identifying further immune cells as cells expressing a second immune cell type specific biomarker; and
  analyzing the at least one received image or the further image of the tissue sample for identifying further tumor cells as cells expressing a second tumor type specific biomarker or using the identified immune cells as further tumor cells;
  for each of the identified further tumor cells, determining the distance of said further tumor cell to the nearest further immune cell; alternatively, for each of the identified further immune cells, the distance of said further immune cell to the nearest further tumor cell is determined;
  computing a further proximity measure as a function of said determined distances;
  in dependence on the further proximity measure, sub-classifying the identified tumor cells and/or predicting the treatability of the tumor by a class of substances.

In a further aspect, the invention relates to an image analysis system for tumor classification, the system being configured for:

receiving at least one digital image of a tissue sample;
analyzing the at least one received image for identifying immune cells and tumor cells in the at least one received image;
for each of the identified tumor cells, determining the distance of said tumor cell to the nearest immune cell;
computing a proximity measure as a function of the determined distances;
in dependence on the proximity measure, classifying the identified tumor cells into tumor cells of an inflammatory tumor or as tumor cells of a non-inflammatory tumor; and
storing the classification result on a storage medium and/or displaying the classification result on a display device.

In a further aspect, the invention relates to a computer readable medium comprising instructions that when executed by a processor causes the processor to execute a method according to any one of the embodiments described herein.

In a further aspect, the invention relates to an image analysis system for tumor classification, the system being configured for:

receiving at least one digital image of a tissue sample;
analyzing the at least one received image for identifying tumor cells in the at least one received image;
analyzing the identified tumor cells for identifying tumor regions, wherein a tumor region is a tissue region whose majority of cells consist of tumor cells;
analyzing the at least one received image for identifying immune cells lying within one of the identified tumor regions or lying within a boundary region around one of the tumor regions, the width of the boundary being smaller than 200 µm; preferentially, the width of the boundary region is between 120 µm and 200 µm; thus, the boundary region may have the shape of a belt surrounding a tumor region, the belt width being the boundary region width.
for each of the identified immune cells, determining the distance of said immune cell to the nearest tumor cell;
computing a proximity measure as a function of the determined distances;
in dependence on the proximity measure, classifying the identified tumor cells into tumor cells of an inflammatory tumor or as tumor cells of a non-inflammatory tumor; and
storing the classification result on a storage medium and/or displaying the classification result on a display device.

Thus, the width of the boundary region around the tumor regions defines the area (tumor region(s) and tumor boundary region(s)) which shall be used for counting individual immune cell-tumor cell distances. Selectively identifying immune cells within the exterior outline of a boundary region around an identified tumor region may allow to ensure that the accuracy of the proximity measure is not negatively affected by including the immune cells that are normally distributed in tissue regions far away from a tumor which would never engage in an immune response against the tumor anyway. In addition, this may ensure that the accuracy of the proximity measure is not negatively affected by a too narrow boundary that would exclude immune cells in close proximity of the tumor whose position is key for predicting the inflammatory status of the tumor.

According to some embodiments, the width of the boundary region is determined for a particular cancer type empirically. The determination comprises: choosing an array of adjacent regions (e.g. circles, squares or rectangles having a predefined diameter, width and/or height e.g. in the range of 20 µm to 40 µm) in the image, the array of adjacent regions starting at a pixel on the tumor region outline ("starting region") and extending at least 200 µm radially away from the tumor center into the non-tumor tissue region (the last one of the adjacent regions being referred to as "terminal region"; counting the number of immune cells in each of said adjacent regions; scanning the immune cell counts of the adjacent regions from the starting region in direction of the terminal region, thereby identifying the first one of the regions lying within a range of 120 µm to 200 µm away from the boundary of the tumor region and basically having the same immune cell count as all subsequently scanned regions. This region is considered to comprise a number of immune cells that is typical for the "normal" non-tumor tissue far away from any tumor tissue; and using the position of the identified region (e.g. a distance of any one of the pixel within said identified region from the pixel on the tumor region outline covered by the "starting region") as the boundary region width.

A "tumor" or "neoplasm" as used herein is an abnormal growth of tissue, and when also forming a mass is commonly referred to as a tumor. This abnormal growth usually but not always forms a mass.

An "inflammatory tumor" as used herein is a tumor against which a localized protective response by the immune system is observable. Said response may comprise the infiltration of plasma cells, lymphocytes, and eosinophils in the tumor.

A "non-inflammatory tumor" as used herein is a tumor where no or no significant response of the immune system against said tumor is observable.

An "immune cell" as used herein is a type of cell formed in the myelopoietic, lymphoid, and reticular portions of the reticuloendothelial system in various parts of the body, and normally present in those sites and in the circulating blood (rarely in other tissues). In particular, the immune cell can be a lymphocyte, e.g. T lymphocytes, B lymphocytes, and macrophages.

A proximity measure is a data value computed from a plurality of immune cell-tumor cell distances. For example, it can be a numerical data value, e.g. a ratio (a value between 0 and 1) of different groups of distances or a slope of a line connecting histogram bins or a data value derived therefrom. The proximity measure may indicate whether the majority of tumor cell-immune cell distances examined is shorter than a predefined distance threshold, e.g. the immunologically effective distance of an immune cell.

An "image analysis system" as used herein is an electronic system, e.g. a computer, configured for extracting meaningful information from digital images by means of digital image processing techniques. Image analysis tasks can comprise color deconvolution, connected component analysis and/or edge detection for identifying cells, for identifying the type of the cells (tumor or stroma cell, different types of immune cells) and distance measurements.

BRIEF DESCRIPTION OF THE DRAWINGS

In the following embodiments of the invention are explained in greater detail, by way of example only, making reference to the drawings in which:

DETAILED DESCRIPTION

Figure 1:
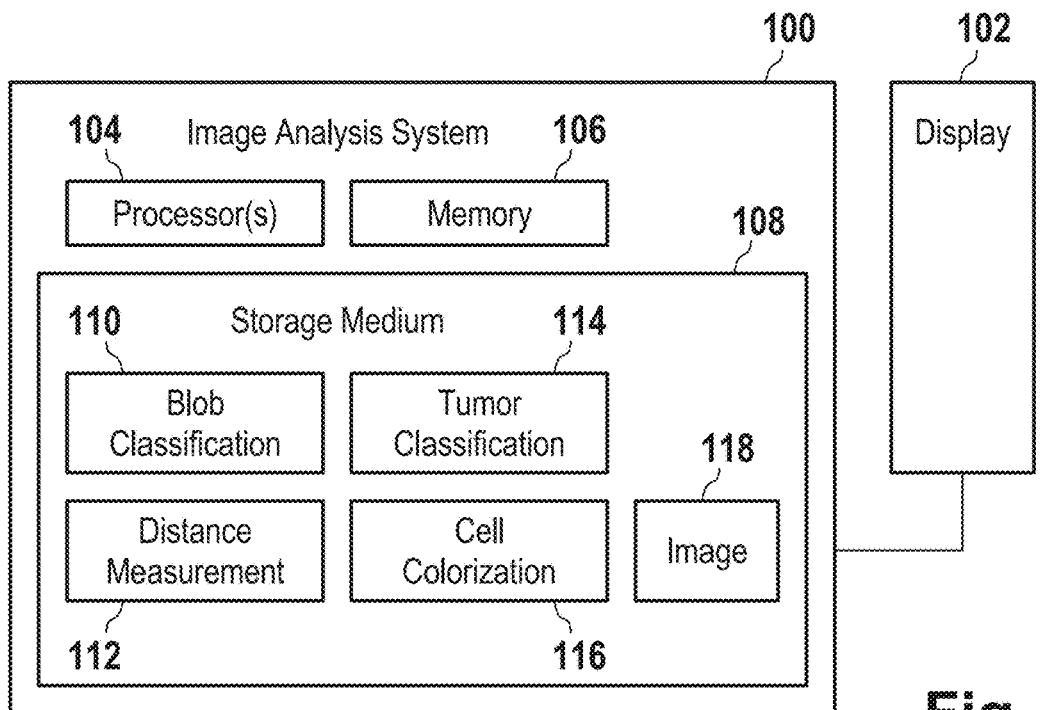
Figure 2:
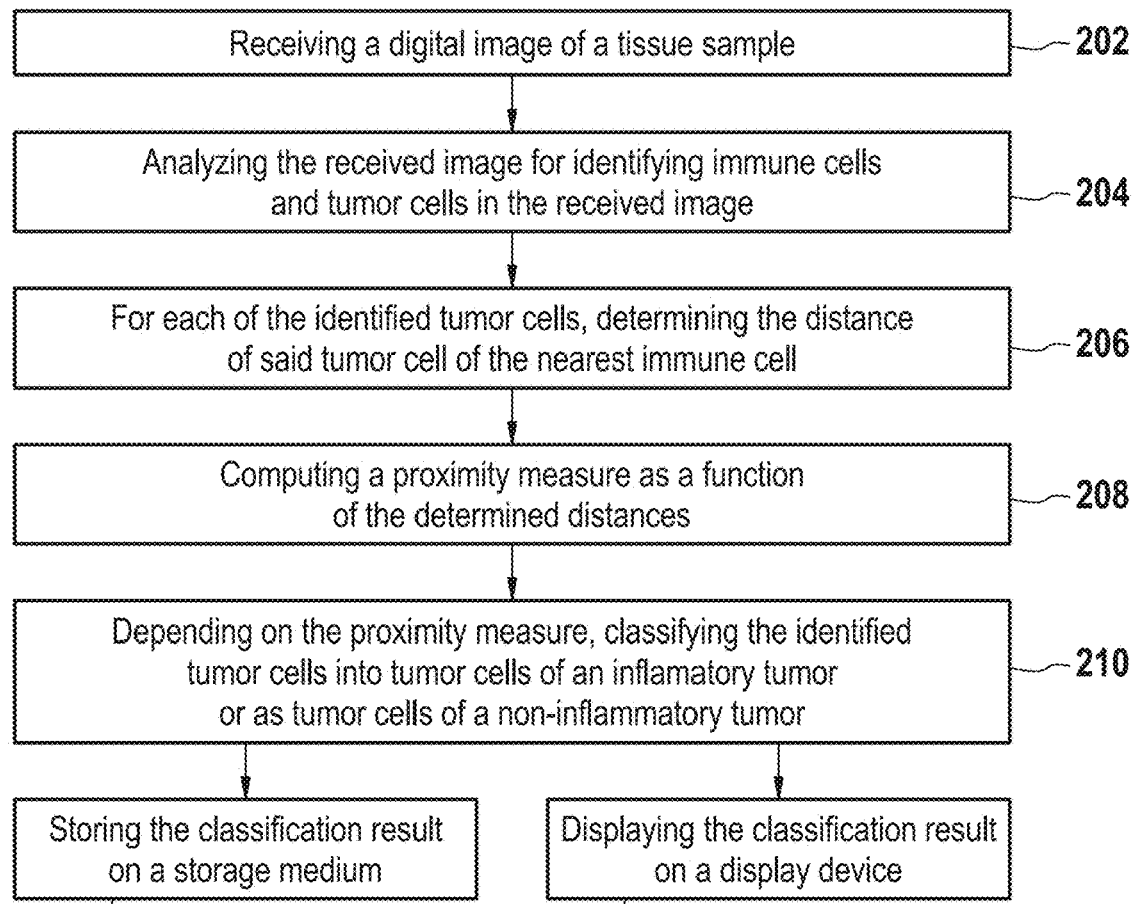
Figure 3:
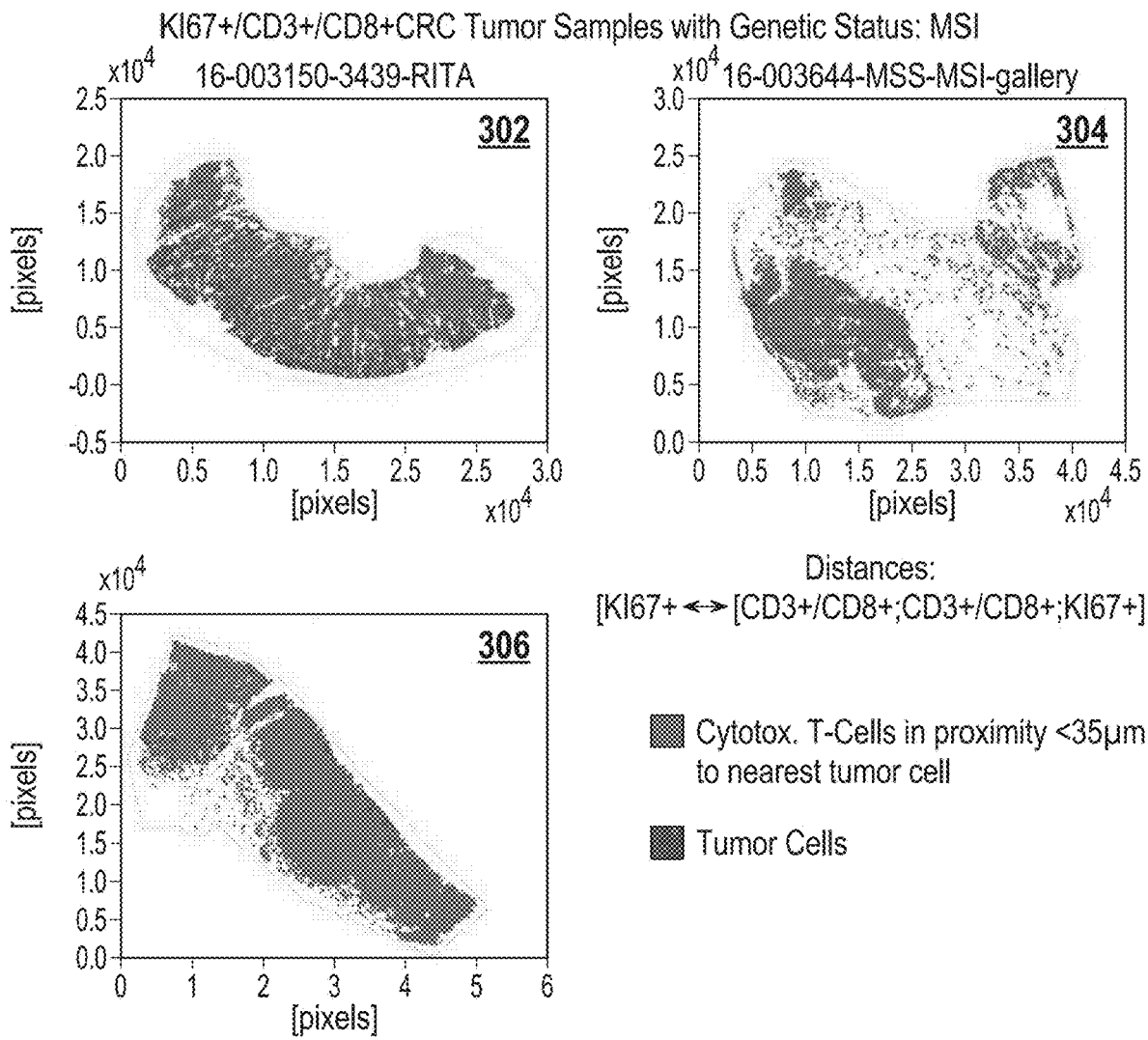
Figure 4A:
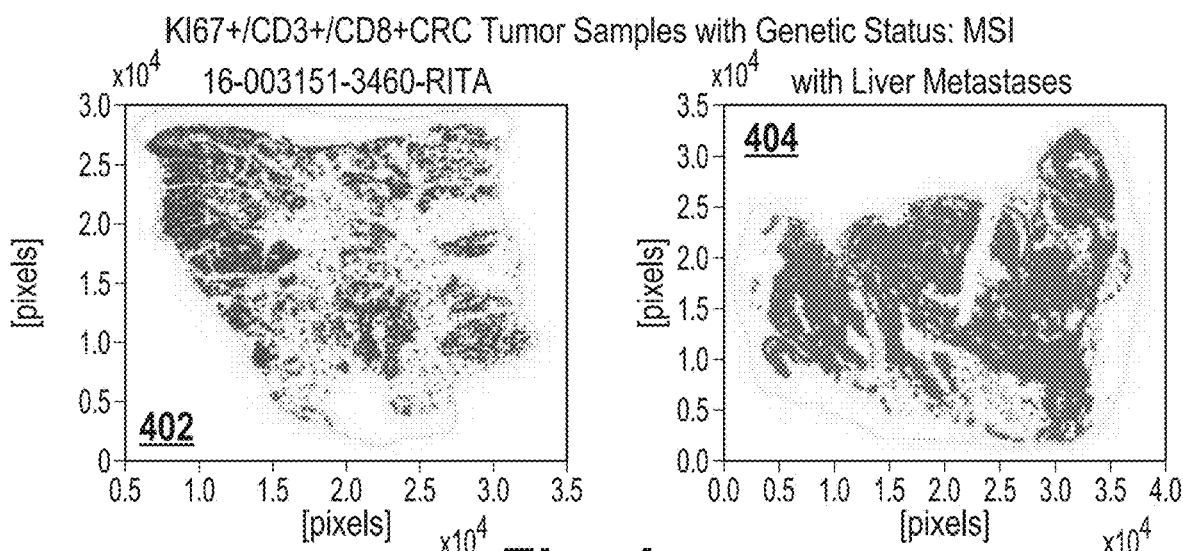
Figure 4B:
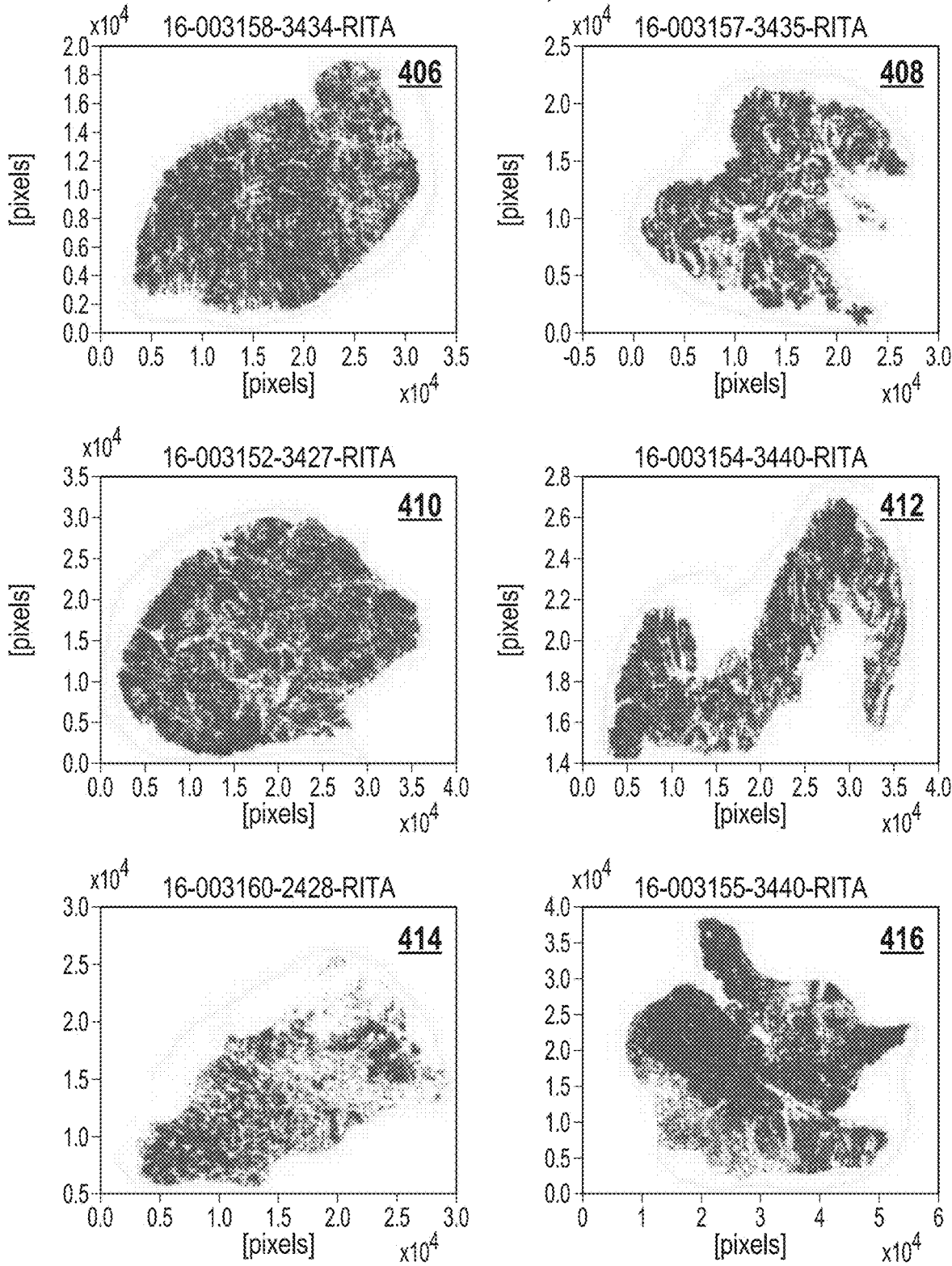
Figure 5:
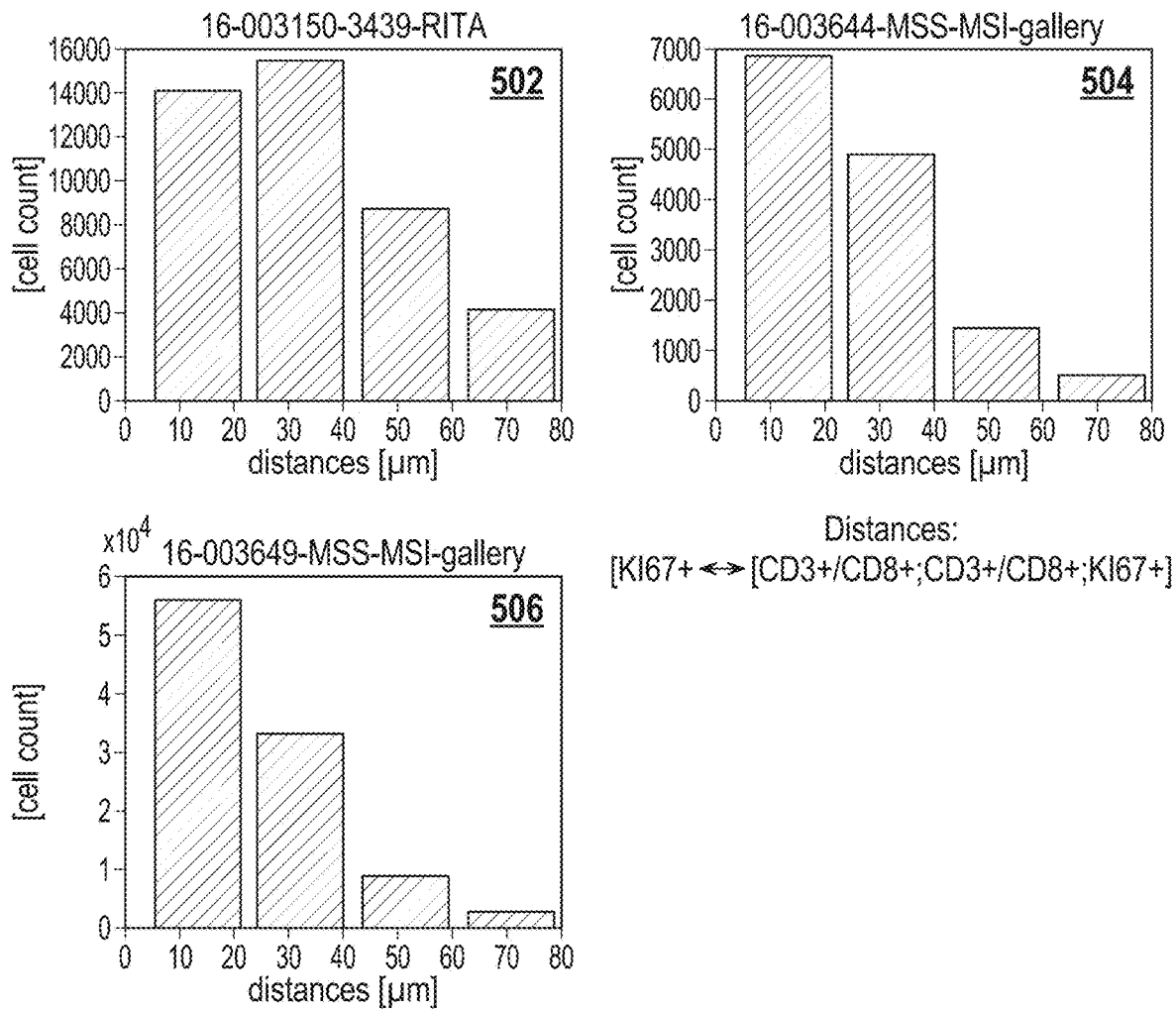
Figure 6A:
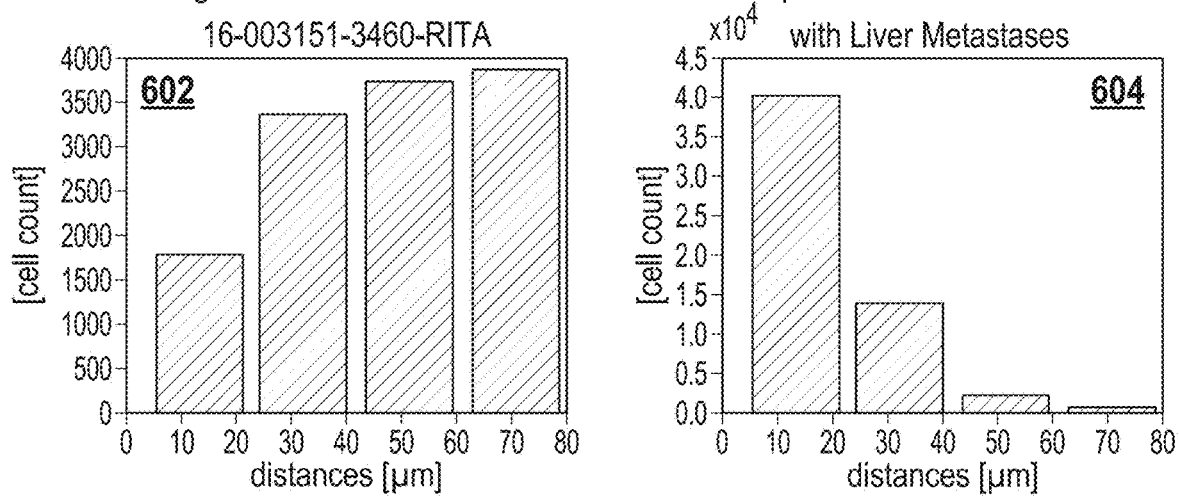
Figure 6B:
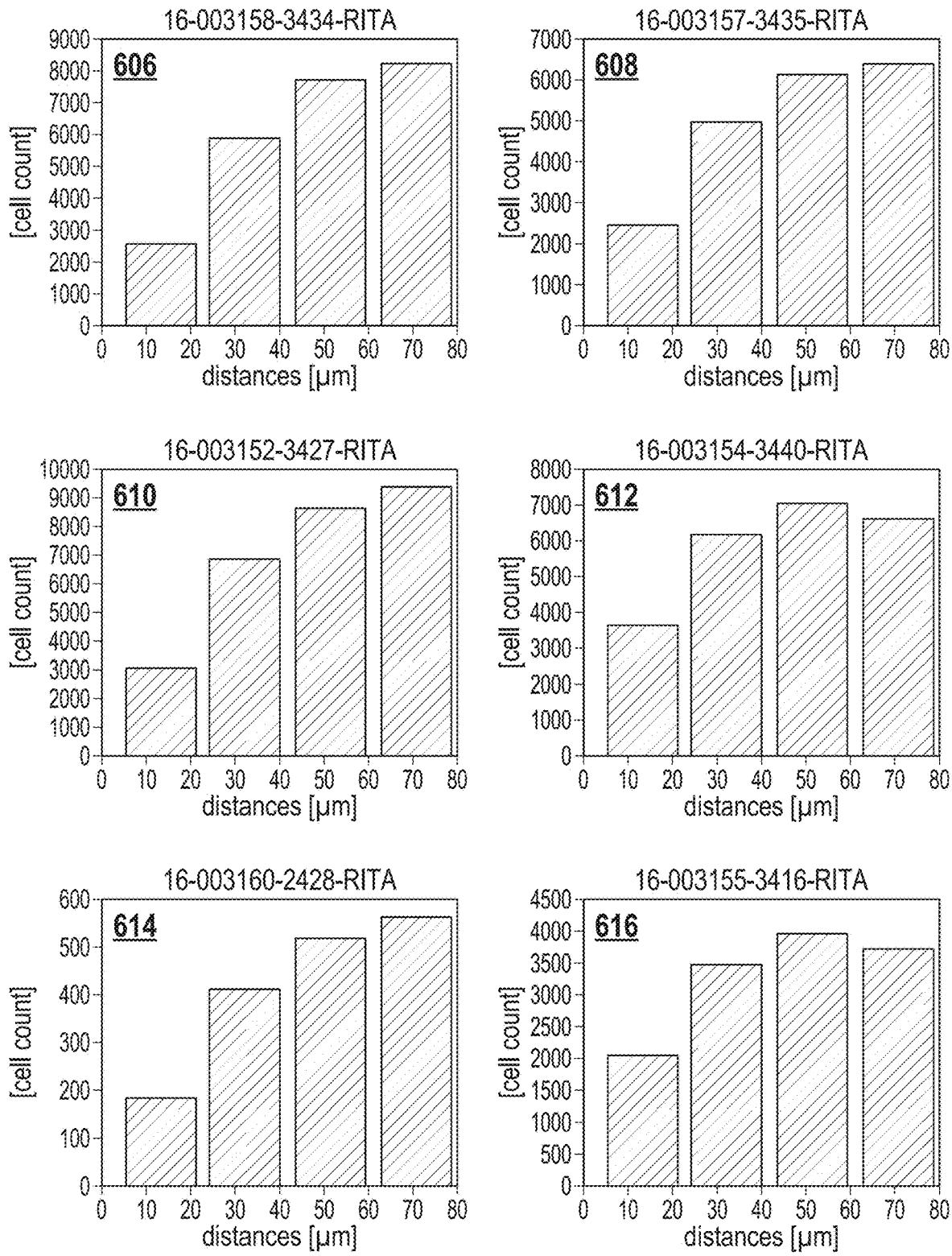
Figure 7:
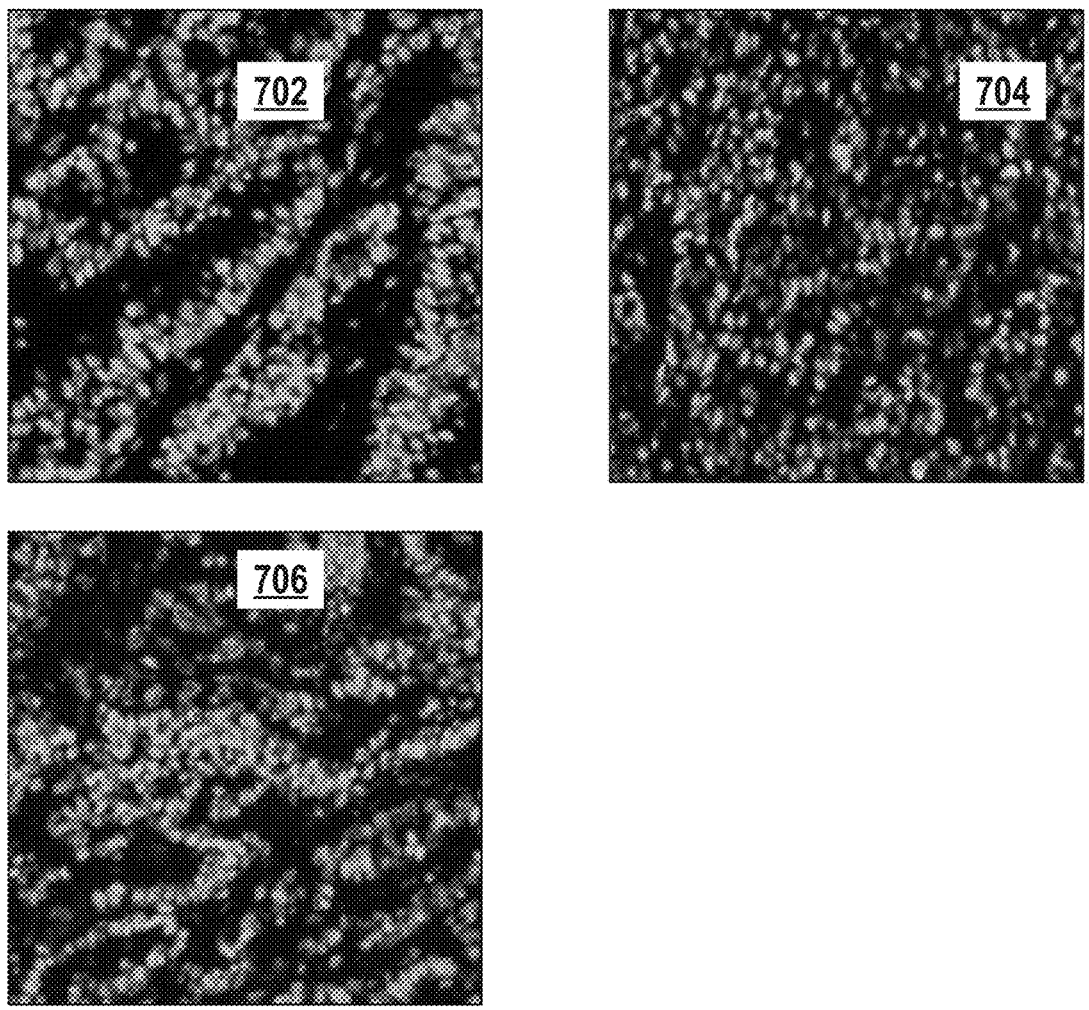
Figure 8A:
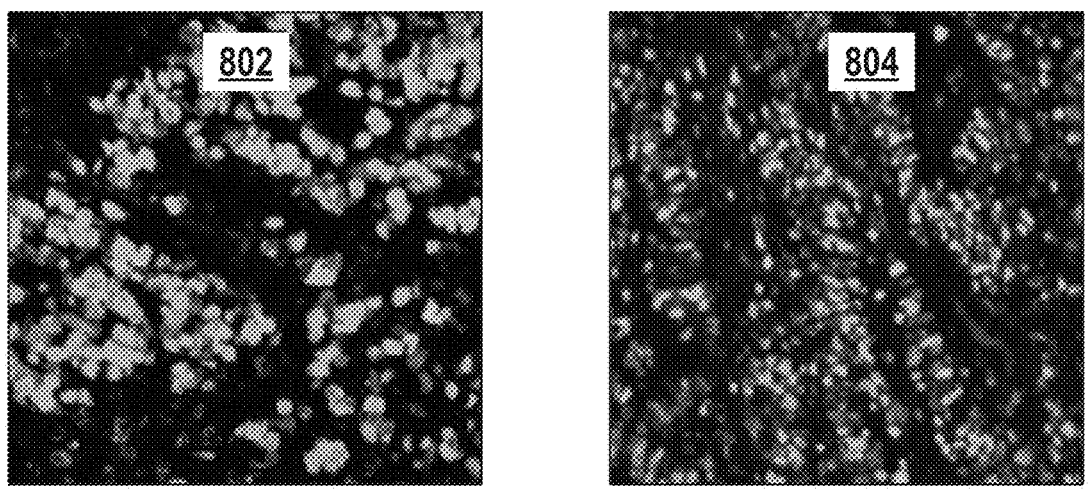
Figure 8B:
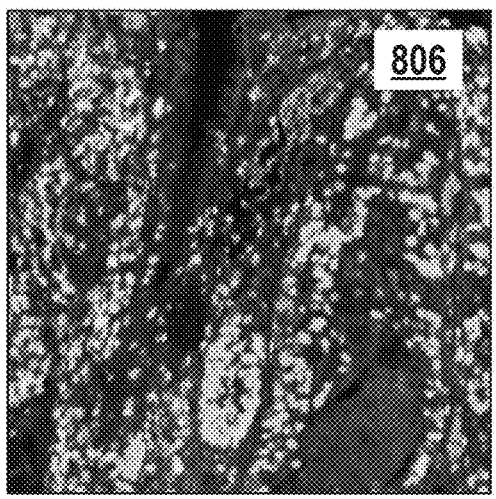
Figure 8B:
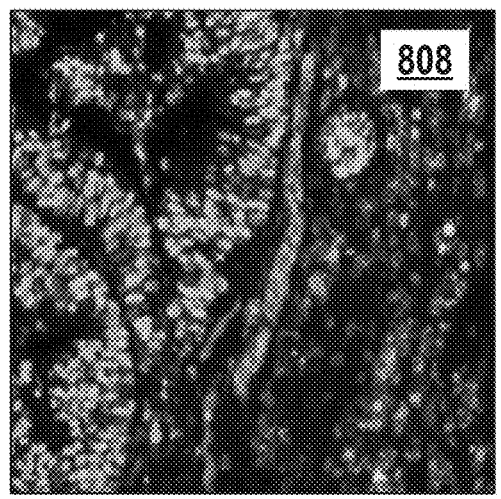
Figure 8B:
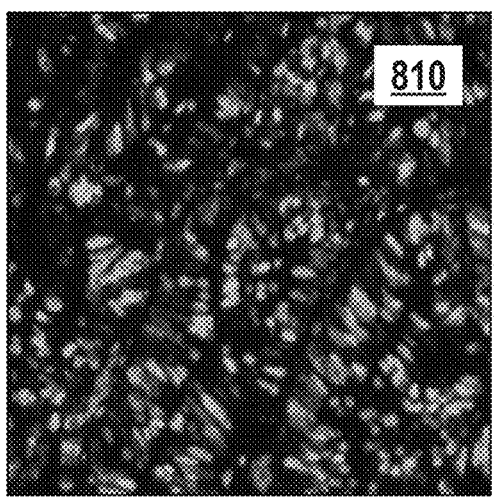
Figure 8B:
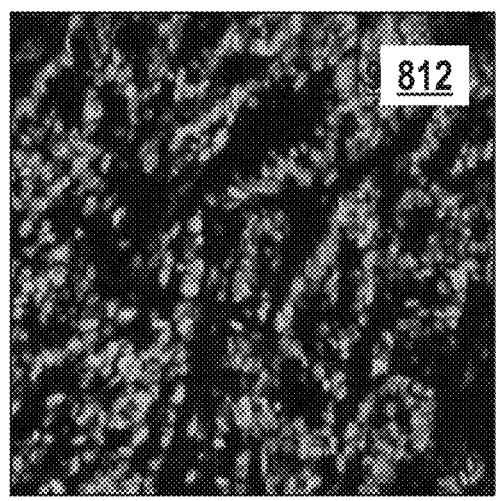
Figure 8B:
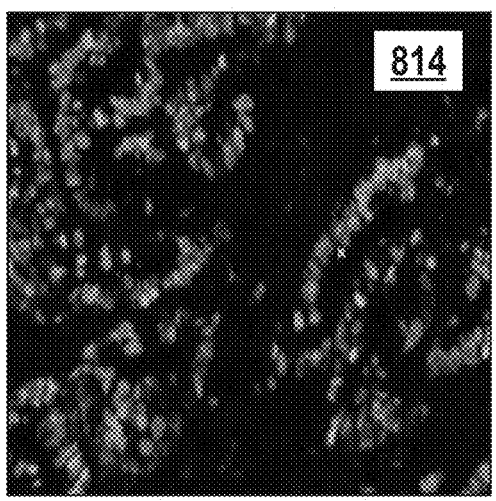
Figure 8B:
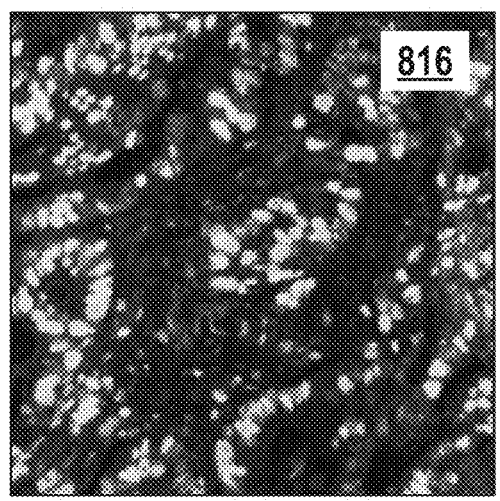
Figure 9:
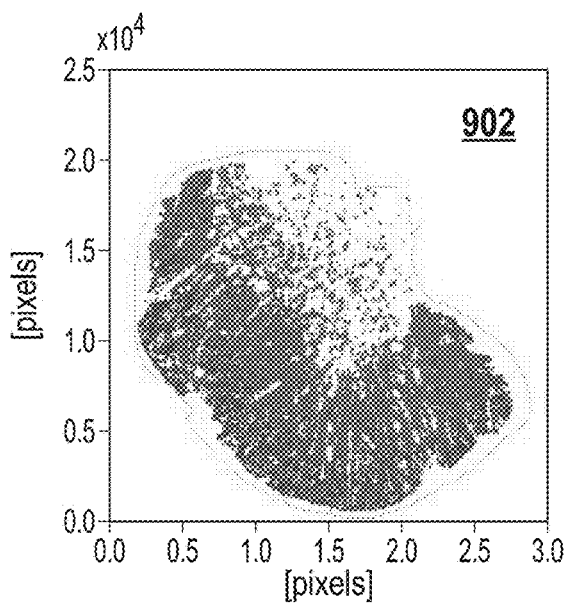
Figure 9:
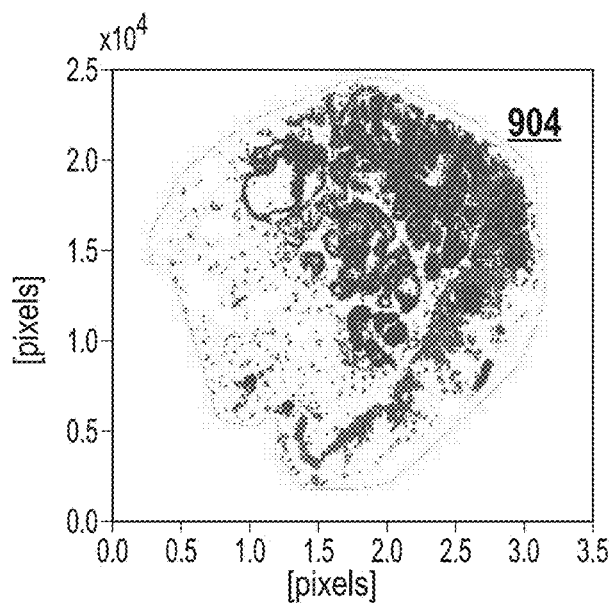
Figure 9:
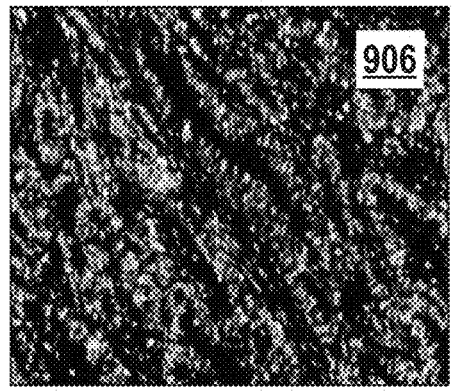
Figure 9:
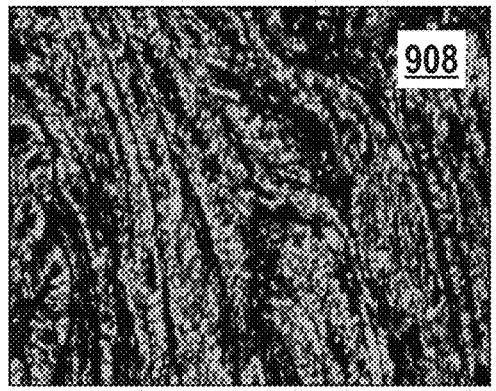
Figure 9:
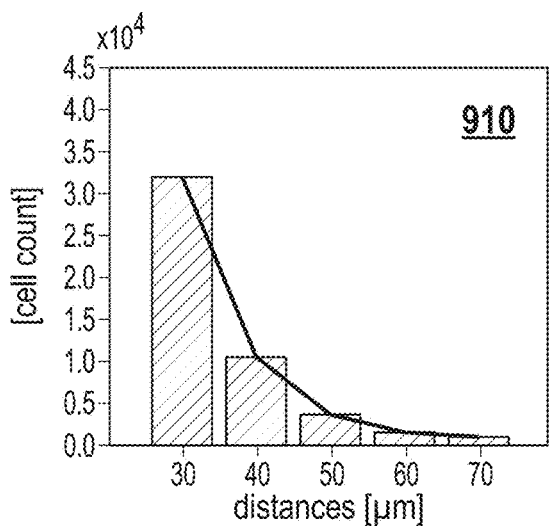
Figure 9:
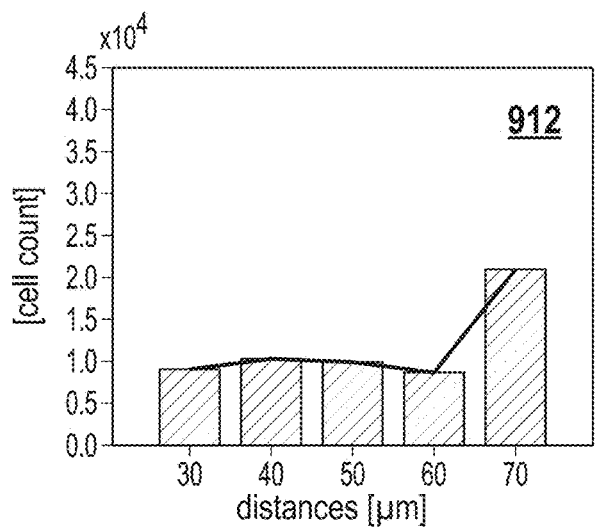
Figure 10:
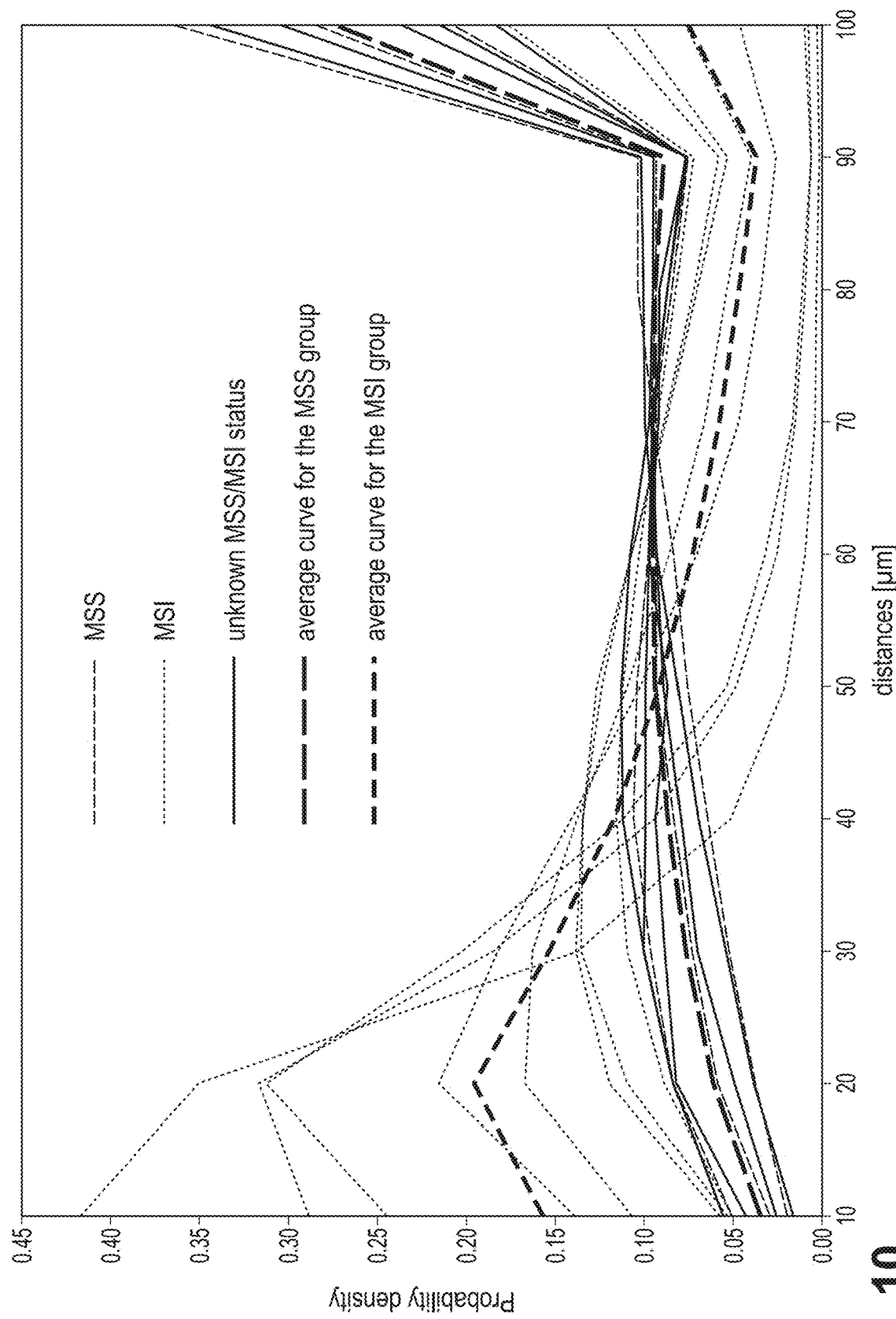

FIG. 1 is a block diagram of an image analysis system;
FIG. 2 is a flow chart of an image analysis method for classifying tumors;

FIG. 3 depicts three overlay images derived from respective MSI tumor samples, the image comprising a first layer with tumor cells and a second layer with differently colored immune cells lying within a maximum distance from the nearest tumor cell;

FIGS. 4a and 4b depict 8 overlay images derived from respective MSS tumor samples;

FIG. 5 depicts three histograms derived from the three MSI tissue samples depicted in FIG. 3;

FIGS. 6a and 6b depict 8 histograms derived from the 8 MSS tissue samples depicted in FIG. 4;

FIG. 7 depicts three IHC fluorescent images of the three MSI tissue samples depicted in FIG. 3;

FIGS. 8a and 8b depict 8 fluorescent images of the 8 MSS tissue samples depicted in FIG. 4;

FIG. 9 depicts a comparison of the overlay image, the IHC fluorescent image and the histogram generated for a MSI sample (left column) and a MSS sample (right column); and FIG. 10 depicts a plot indicating the probability density that a particular immune cell lies within a given distance from its nearest tumor cell.

Figure 11:
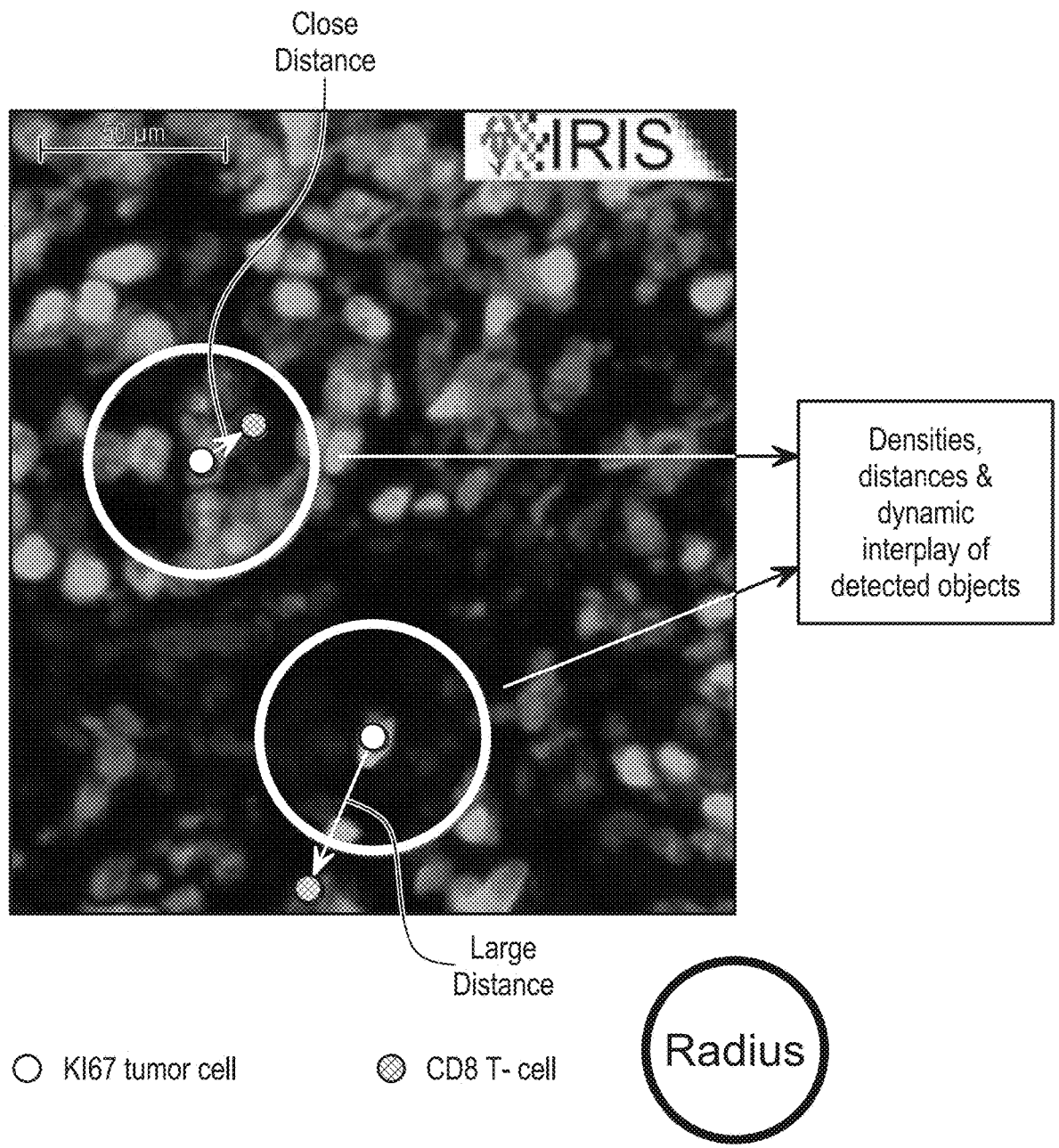

FIG. 11 depicts the combination of proximity information and cell density information for capturing tumor context information for classifying the tumor.

Figure 12:
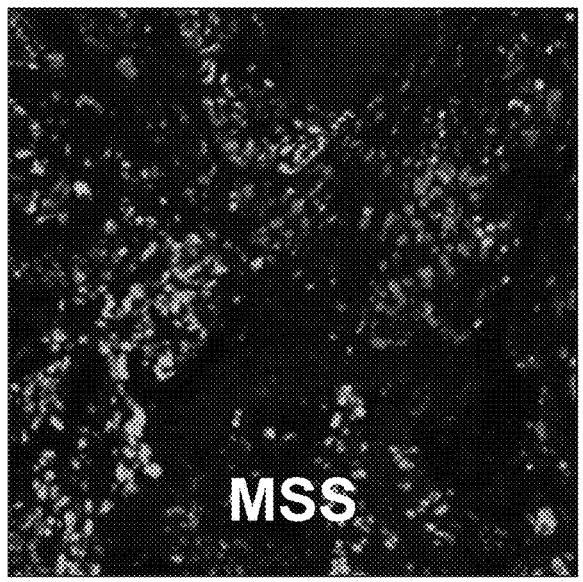
Figure 12:
Figure 12:
Figure 12:
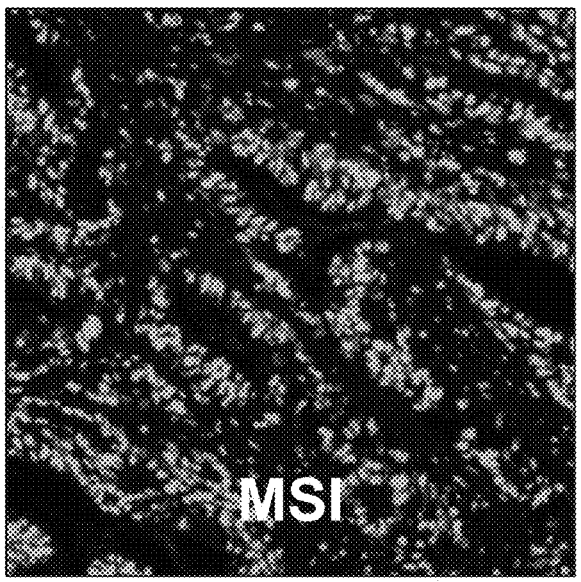
Figure 12:
Figure 12:

FIG. 12 depicts stained tissue samples of two patients having similar T-cell densities but different proximity measures.

FIG. 1 is a block diagram of an image analysis system 100 according to an embodiment of the invention. The system comprises one or more processors 104, a main memory 106 and a non-volatile storage medium 108. The storage medium comprises one or more application programs or modules 110, 114, 112, 116 configured for performing one or more image processing tasks. For example, a first module 110 may perform a connected component analysis and edge detection routines in order to identify pixel blobs representing cells. The identification may be performed on different monochromatic fluorescent or brightfield microscopy images having been derived from the same tissue sample whereby the pixel intensities of the different monochromatic images respectively are indicative of a particular biomarker. Multiple monochromatic fluorescent images can be derived from a multispectral fluorescent image of a particular tissue sample by applying a color deconvolution algorithm.

The storage medium 108 may further comprise one or more digital images 118 of a tissue sample having been stained with one or more biomarker specific stains. Moreover, the system 100 is coupled to or comprises a display 102, e.g. an LCD display. The system uses the display 102 for displaying the digital images 118 of tissue samples of various patients (see for example FIGS. 7 and 8), for displaying overlay images (as shown for example in FIGS. 3 and 4) having been derived from various tissue images 118, for displaying a graphical representation of proximity measures (for example histograms depicted in FIGS. 5 and 6) and/or for displaying a tumor classification result or treatment suggestion.

For example, a tissue sample, e.g. a biopsy sample, is used that has been stained by a plurality of biomarker specific stains. One or more of that stains selectively bind to strongly proliferating non-lymphoid cells or to proteins selectively expressed by tumor cells. Intensity signals of said stains and the corresponding monochromatic images can be analyzed by module 110 for identifying tumor cells. One or more further ones of said stains selectively bind to immune cells or specific subtypes of immune cells, e.g. cytotoxic t cells or T-helper cells. Intensity signals of said stains and the corresponding monochromatic images can be analyzed by module 110 for identifying immune cells. After having executed application program or module 110, tumor cells and immune cells within a tissue sample and the corresponding digital images have been identified.

Then, a distance measurements application program or module 112 uses the location of the pixel blobs identified as immune cells and tumor cells as input for determining the distance of tumor cells and their closest neighboring immune cells. For example, module 112 identifies the center of each cell and determines the distance between the respective cell centers. Alternatively, module 112 determines the distance as the distance between the outer boundaries of the two neighboring cells.

The totality of distances measured by module 112 is provided as input to the application program or module 114 which computes a proximity measure as a function of the totality of distances provided by module 112 for a particular tissue sample. The module 114 computes, for example, a ratio between tumor cells for which at least one immune cell within a predefined distance threshold was identified and tumor cells for which no immune cells within that predefined distance threshold was identified. In addition, or alternatively, module 114 may compute a histogram for all identified distances between any of the tumor cells and its nearest immune cell neighbor and may compute a slope of the histogram bins as illustrated by FIGS. 5, 6 and 9.

In addition, the totality of distances measured by module 112 is provided as input to the application program or module 116 which generates an overlay image as depicted, for example, in FIGS. 3 and 4. In an overlay image tumor cells are represented in a base image layer in a first color and immune cells having been identified as being the next neighbor to at least one of the tumor cells and having in addition been identified as lying within a distance from said tumor cell that is below a distance threshold (e.g. a predefined "immunologically effective distance") are represented in a further image layer in a second color. The further layer is presented on top of the base layer. The images 118, the colorized overlay image is generated by module 116 and/or the histograms are presented to a user, e.g. a pathologist, via display 102.

FIG. 2 is a flow chart of an image analysis method for classifying tumors. The methods depicted in FIG. 2 can be implemented, for example, by an image analysis system 100 as depicted in FIG. 1.

In a first step 202, the image analysis system receives a digital image 118 of a tissue sample. The digital image can be a multispectral fluorescent immunohistochemistry (IHC) image that is decomposed by the image analysis system into a plurality of monochromatic images by applying a color deconvolution algorithm. Alternatively, the image analysis system may receive a plurality of monochromatic digital images of the tissue sample. The multispectral digital image and/or the plurality of monochromatic digital images of the tissue sample can be provided via an interface with an image acquisition system. Alternatively, the image analysis system 100 may receive the digital images of the tissue sample by reading the images from a storage medium, e.g. a CD-ROM or flash drive.

For example, the tissue sample from which the images where derived can be a biopsy of a colorectal cancer tissue sample having being stained by a plurality of fluorescent stains selectively binding the following biomarkers: KI67, CD3 and CD8. Pixel regions for which a KI67 signal but no CD3 or CD8 signal was obtained are identified as proliferating non-lymphoid cells and thus are identified as tumor cells. Pixel regions for which a CD3 and a CD8 signal was obtained are identified as cytotoxic T-cells and thus are identified as immune cells. A "KI67 signal" as used herein is a light signal emitted by a stain that selectively stains the KI67 protein, whereby said light signal is represented in the form of pixel intensity values in a respective monochromatic image that selectively captures the emission spectrum of the stain used for selectively staining the KI67 protein. This definition applies analogously also to the other "biomarker signals".

For example, digital images of IHC-stained glass slides can be acquired using a Ventana iScan HT Slide Scanner. Images were viewed and organized using the Roche IRIS Platform. Ventana image analysis software VDP-SKD and the Ventana Digital Pathology Software Development Kit was used for performing most of the image analysis methods for identifying the cell boundaries and for identifying separate tissue and glass regions, tumor cells and immune cells and tumor cell regions mainly (e.g. to more than 50%) consisting of tumor cells.

In a second step 204, module 110 of the image analysis system performs one or more image analysis routines for identifying immune cells and tumor cells in the received digital image or images of the tissue sample. Image analysis routines for detecting cells, e.g. via a connected component analysis, gray scale and color segmentation techniques, intensity thresholding and the like are known in the art.

In a further step 206, module 112 of the image analysis system determines, for each of the identified tumor cells, the distance of the tumor cell to the nearest immune cell, e.g. by measuring the distance between cell boundaries.

After step 206 has completed, module 114 computes a proximity measure as a function of the determined distances in step 208. For example, the proximity measure can be a ratio of tumor cells having at least one "near immune cell" and of tumor cells not having such a "near immune cell", whereby a "near immune cell" is a immune cell lying within a predefined (e.g. immunologically effective) maximum distance from a tumor cell. In other words, this ratio describes the ratio of tumor cells that can potentially be attacked by a nearby immune cell and those tumor cells which appear not to be attackable by an immune cell. In addition, or alternatively a slope of two or more bins of a distance histogram can be computed, whereby a negative slope (from short distance bins to long distance bins) indicates that the majority of tumor cells can potentially be attacked by a nearby immune cell and whereby a positive slope (from short distance bins to long distance bins) indicates that the majority of tumor cells can probably not be attacked successfully by an immune cell.

In step 210, module 114 classifies the identified tumor cells into tumor cells of an inflammatory tumor or as tumor cells of a non-inflammatory tumor in dependence on the proximity measure. For example, if the ratio is larger than 1 and/or if the slope is negative, the tumor cells are classified as inflammatory tumor cells. If the ratio is smaller than 1 and/or if the slope is positive, the tumor cells are classified as non-inflammatory tumor cells.

In step 212, the classification result is stored on a storage medium 108. In addition, or alternatively, the classification result is displayed on a display device 102. For example, an overlay image is depicted in FIGS. 3 and 4 can be used as graphical representation of the classification result: if the majority of tumor cells are covered by an immune cell being within the "immunologically effective distance", this is an indication that the tumor cell is depicted in the overlay image is a tumor cell of an inflammatory tumor.

FIGS. 3 and 4 depict overlay images generated for a group of colorectal cancer (CRC) patients. Using an immunofluorescence assay (CD3/CD4/CD8/Ki67/DAPI), surgical samples obtained from primary tumors of colorectal cancer (CRC) patients (n=23) was stained. The MSS/MSI status of said patients was known. KI67+/CD3− cells were identified as tumor cells. CD3+/CD8+ cells were identified as immune cells.

FIG. 3 depicts three overlay images 302-306 computed by the image analysis system for three of the CRC patients whose microsatellite stability status was identified as "instable" ("MSI").

Each of the images comprises a first layer wherein all tumor cells are colorized with a first color, e.g. blue, irrespective of the presence or location of any immune cell. In each of said images 302-306, said first layer is overlaid with (and covered by) a second layer with pixel blobs representing immune cells having been identified as lying within a predefined maximum distance from at least one tumor cell. For example, these "potentially immunologically effective" immune cells are colorized in orange. It is important to note that the second layer does not indicate the presence of immune cells not lying within the predefined maximum distance. Thus, the second layer is not simply an overlay of layers representing immune cells and tumor cells in different colors, but rather is a computational result being indicative of potentially immunologically effective immune cells within the tumor. It has been observed that this particular form of overlay image provides a better and more accurate indication regarding the inflammatory state of a tumor than a mere superposition of a generic tumor cell image layer and a generic immune cell image layer.

As can be seen from FIG. 3, the majority of tumor cells in each of the overlay images 302, 304, 306 is covered by "potentially immunologically effective immune cells". The most complete coverage is observed in image 306. Thus, the tumor cells of the tissue samples corresponding to overlay images 302-306 are classified as cells of an inflammatory tumor. Thus, for those three patients, the status "MSI" is "in line" with the distance-based classification result.

FIG. 4 depicts 8 overlay images derived for 8 other patients whose microsatellite stability status is "stable" (MSS). The overlay images were generated as already described for FIG. 3. The overlay images 402, 406-416 clearly show that the majority of tumor cells is not covered by pixels representing a "potentially immunologically effective" immune cell, i.e., an immune cell lying within a predefined maximum distance from at least one tumor cell. Thus, the tumor cells of the tissue samples corresponding to overlay images 402, 406-416 are classified as cells of a non-inflammatory tumor. For the corresponding seven patients, the status "MSS" is "in-line" with the distance-based classification result.

However, in the overlay image 404 the tumor cells are almost completely covered by "potentially immunologically effective" immune cells. Thus, the image analysis system according to embodiments of the invention the classifies the tumor cells of the tissue sample depicted in overlay image 404 as tumor cells of an inflammatory tumor. This is in contradiction to the known genetic MSS status of the corresponding patient. An in-depth analysis by a pathologist revealed that indeed the tumor depicted in overlay image 404 was an inflammatory tumor. If the MSS/MSI status would be used as a basis for a treatment decision, the corresponding patient would not have been prescribed a drug that stimulates or modulates an immune response. However, using a proximity measure as described herein for embodiments of the invention as a basis for a treatment suggestion, the patient corresponding to overlay image 404 is identified by the image analysis system as a patient benefiting from the subscription of a dragon that stimulates the immune system.

FIG. 5 depicts three histograms 502, 504, 506 derived from the same three MSI tissue samples whose computed overlay images 302, 304, 306 are depicted in FIG. 3.

Each histogram depicted in FIGS. 5, 6 and 9 comprises four distance bins. The first been covers a distance of 0 μm to 20 μm, the second been covers a distance from 21 μm to 40 μm, the third been covers a distance of 41 μm to 60 μm and the last bin covers a distance from 61 μm to 80 μm. The term "distance" relates to the distance of anyone of the identified tumor cells to its nearest identified immune cell. The distance refers to the "real" distance between respective cells in the tissue sample.

The image analysis system uses information on the resolution and/or zoom factor of the image as input for computing the cell-cell distance in μm from the numbers of pixels separating the boundaries of two cells within one image. For each bin, a corresponding bar is plotted in the histogram, whereby the height of each bar reflects the number of tumor cells whose distance to its nearest immune cell falls within said bin.

As can be inferred from the histograms 502, 504, 506, the majority of tumor cells is contained in the first and second been representing distances within the immunologically effective distance of immune cells. By plotting a straight or curved line that connects the top of the bar of the first bin with the top of the bar of the last bin and by determining the slope of that line, a negative (falling) slope will be identified. A negative slope in the distance histogram is used as a proximity measure that indicates that the tumor cells of the tumor belong to an inflammatory tumor. This proximity measure based classification result is in line with the microsatellite instability status information "MSI".

FIG. 6 depicts 8 histograms derived from the 8 MSS tissue samples whose overlay images are depicted in FIG. 4. Thus, the histograms 602-616 correspond to the 8 patients whose microsatellite stability status is "stable" (MSS). The histograms were generated as already described for FIG. 5. The histograms, 602, 606-616 all have a positive slope, thereby clearly showing that the majority of tumor cells does not comprise a neighboring immune cell within the predefined maximum distance that reflects the "immunologically effective" immune cell distance. Thus, the tumor cells of the tissue samples corresponding to histograms 602, 606-616 are classified as tumor cells of a non-inflammatory tumor. For the corresponding seven patients, the status "MSS" is "in-line" with the slope-based classification result.

However, in histogram 604 (corresponding to the same patient as overlay image 404), a negative slope is observed and the image analysis system classifies the tumor cells of the tumor corresponding to the distance histogram 604 as an inflammatory tumor. This is in contradiction to the known genetic MSS status of the corresponding patient. As was explained above, the in-depth analysis revealed that indeed the tumor corresponding to histogram 604 was an inflammatory tumor.

In other words, the proximity measure based tumor classification, e.g. the tumor cell ratio based classification illustrated in FIG. 3 and four as well as the histogram slope based classification illustrated in FIG. 5 and six a more accurate than state-of-the-art MSS/MSI status based tumor classification.

FIG. 7 depicts three IHC fluorescent images 702, 704, 806 of the MSI tissue samples of the three patients for which respective overlay images were generated as depicted in FIG. 3 and for which respective distance histograms were generated as depicted in FIG. 5.

FIG. 8 depicts 8 IHC fluorescent images 802-816 of the MSI tissue samples of the 8 patients for which respective overlay images were generated as depicted in FIG. 4 and for which respective distance histograms were generated as depicted in FIG. 6. IHC image 804 shows the inflammatory tumor whose IHC image looks more similar to the IHC images 702-706 than to IHC images 802, 806-816.

FIG. 9 depicts a comparison of two groups of images, wherein the group depicted on the left corresponds to an inflammatory CRC tumor of a first patient and the group to the right corresponds to a non-inflammatory CRC tumor of a second patient. Tumor cells were identified as KI67+/CD3− cells. Immune cells (here: cytotoxic T-cells) were identified as CD8+/CD3+ cells. The first (topmost) row depicts overlay images computed in the same way as described for FIGS. 3 and 4. The second row depicts the IHC fluorescent images of the respective tissue samples and the third row depicts the respectively computed distance histograms generated as described for FIGS. 5 and 6.

For inflammatory tumor tissue (left column), the majority of tumor cells are covered in the overlay image 902 by immune cells having been identified to lie within a predefined maximum distance (immunologically effective distance) from a tumor cell. A corresponding field of view (FOV) 902 from the corresponding tissue below sows a significant degree of tumor immune infiltration. The slope of the corresponding distance histogram determined as described for FIGS. 5 and 6 is negative.

For non-inflammatory tumor tissue (right column), the majority of tumor cells are not covered in the overlay image 904 by immune cells having been identified to lie within a predefined maximum distance (immunologically effective distance) from a tumor cell. A corresponding field of view (FOV) 908 from the corresponding tissue below sows that there is almost no tumor infiltration by immune cells will. The slope of the corresponding distance histogram determined is positive.

The difference in distribution of cytotoxic t cells engaging cancer cells between different tumor categories as expressed graphically in the overlay images 902, 904 and as expressed in the slope of the histograms 910, 912 is apparent.

FIG. 10 depicts a plot indicating the probability density that a particular immune cell lies within a given distance from its nearest tumor cell.

A probability density function (PDF) is a function that describes the relative likelihood for a variable to take on a given value. The probability of the variable falling within a particular range of values is given by the integral of this variable's density over that range—that is, it is given by the area under the density function but above the horizontal axis and between the lowest and greatest values of the range. The probability density function is nonnegative everywhere, and its integral over the entire space is equal to one.

The plot depicts multiple thin MSS curves respectively representing the probability function in dependence on the distance of a tumor cell to its nearest immune cell obtained from an image of a tissue sample having been classified as MSS sample. For the MSS samples, the probability density strongly increases at a distance larger than 90 μm. A bold MSS curve represents the average of all MSS curves in the plot.

The plot further depicts multiple thin MSI curves respectively representing the probability function in dependence on the distance of a tumor cell to its nearest immune cell obtained from an image of a tissue sample having been classified as MSI sample. For the MSI samples, the probability density is highest at a distance smaller than 35 μm. A bold MSI curve represents the average of all MSI curves in the plot.

In addition, the plot comprises some curves obtained for tissue samples with unknown MMS/MSI status.

The automated evaluation of tumor cell-immune cell distances in a tissue sample on a whole slide level provides a more comprehensive and accurate insight into tumor biology.

FIG. 11 depicts a digital image of a stained colorectal cancer sample comprising annotations of tumor context information. A combination of proximity information and cell density information is captured as tumor context information for classifying the tumor. As was described for several embodiments of the invention, proximity measures between tumor cells and immune cells have been observed to represent valuable predictive parameters for classifying tumor cells into tumor cells of an inflammatory tumor or as tumor cells of a non-inflammatory tumor. The classification result may also be used for predicting whether or not the tumor will be treatable by a drug that boosts the immune system. Thus, the distances between immune cells and tumor cells and the distance measure derived therefrom represent tumor context information that provides valuable predictive information on the likely tumor type, tumor progression and treatability.

It has been observed that the accuracy of the classification can significantly be increased by determining and using as input also the density of the tumor cells and/or the density of immune cells. Thus, according to embodiments, the tumor cell density and/or the immune cell density (measured e.g. in number of cells per 100 μm×100 μm) is automatically determined and is fed as an additional input to the classifier. According to embodiments, the density of the immune cells is determined in an immune cell type specific manner (resulting in the computation of a density of cytotoxic t-cells, a density for macrophages, a density for B-cells, etc.).

Accordingly, in the training phase of the classifier, density information can be assigned to each tumor cell and/or to each immune cell contained in any of the training images. For example, for each tumor cell in a training image, a square-shaped or circular area of about 100 μm×100 μm comprising said tumor cell in its geometrical center may be determined. Then, the number of tumor cells in said area is automatically determined and the tumor cell density is computed for said area. Then, the computed density is assigned to the tumor cell in the center of the area. This procedure may be repeated for each tumor cell. Likewise, for each immune cell in the training image, a square-shaped or circular area of about 100 μm×100 μm comprising said immune cell in its geometrical center may be determined. Then, the number of immune cells in said area is automatically determined and the immune cell density is computed for said area. Then, the computed density is assigned to the immune cell in the center of the area. According to embodiments, the density of the immune cells is determined in the training phase in an immune cell type specific manner (resulting in the computation of a density of cytotoxic t-cells, a density for macrophages, a density for B-cells, etc.).

In the depicted image, several tumor cells (Ki67 positive cells) and several immune cells (CD8 positive T-cells) were identified and the distance between the tumor cells and the T-cells was determined (see the large two circles around the two small tumor cells): each of the large circle represents a distance threshold of e.g. about 35 μm. For each of the identified tumor cells, the image analysis system determines the distance of said tumor cell to the nearest immune cell and determined if said distance is below the predefined distance threshold indicated by the large circles. The ratio of tumor cells for which a "close distance" smaller than the distance threshold and tumor cells for which a "large distance" larger than the distance threshold was measured is fed in addition to e.g. immune cell density information of the respective tumor cells into the classifier for classifying a tumor as "inflammatory" or "non-inflammatory".

According to embodiments, the classifier is configured such that the classification of the identified tumor cells into "tumor cells of an inflammatory tumor" or as "tumor cells of a non-inflammatory tumor" comprising checking if the tumor cell densities of the majority of the tumor cells in the tumor depicted in the received image are within a tumor cell density range that is expected for a tumor cell of an inflammatory tumor or if the tumor cell densities of the majority of the tumor cells in the tumor depicted in the received image are within a tumor cell density range that is expected for a tumor cell of a non-inflammatory tumor. For example, the expected density ranges can be specified manually for different types of tumors (inflammatory/non-inflammatory breast cancer/colon cancer/lung cancer etc) or can be specified automatically and implicitly during the training phase by using the tumor cell densities as additional training parameters.

In addition or alternatively, the classifier is configured such that the classification of the identified tumor cells into "tumor cells of an inflammatory tumor" or as "tumor cells of a non-inflammatory tumor" comprising checking if the immune cell densities of the majority of the immune cells in spatial proximity to the tumor are within an immune cell density range that is expected in the context of an inflammatory tumor or if the immune cell densities of the majority of the immune cells in spatial proximity to the tumor are within an immune cell density range that is expected in the context of a tumor cell of a non-inflammatory tumor. As mentioned above, the expected density ranges for the immune cell densities can be specified manually for different types of tumors (inflammatory/non-inflammatory breast cancer/colon cancer/lung cancer etc) or can be specified automatically and implicitly during the training phase by using the immune cell densities as additional training parameters.

According to embodiments, the proximity measures and the cell densities are determined multiple times before, during and/or after the treatment of a patient for predicting the treatability of a tumor and for determining whether or not an applied drug had an effect on the tumor or the immune cells.

Moreover, according to embodiments, the dynamic interplay of any cell population (e.g. tumor cells or immune cells) with a given reference point (e.g. a cell of another cell type than that of the cell population like immune cells, tumor cells, stroma cells or other tissues, e.g. vessels) is determined and used as an additional predictive input parameter for training an untrained classifier and/or for feeding a trained classifier.

FIG. 12 depicts stained tissue samples of two patients A, B having similar T-cell densities but different proximity measures. Different degrees of immune cell infiltration in tumor nests have been observed to represent important signs of tumor cell recognition and/or eradication by immune cells. In the two compared tissue samples, the same T-cell density but strongly deviating proximity measures were observed: while in sample A only 4% of the tumor cells were observed in close proximity to a T-cell, in sample B more than 20% of the tumor cells had at least one T-cell in close proximity, e.g. within a distance of about 35 µm. It has been observed that a low degree of tumor infiltration by immune cells correlates with a microsatellite status "MSS" while a high degree of tumor infiltration (sample B) correlates with a microsatellite status "MSI". Moreover, it has been observed that while already the computation of the proximity measure provides good or even better inflammatory/non-inflammatory tumor classification results than the conventional and expensive determination of MSS/MSI state, it has been observed that the additional determination and use of density information provides significantly more accurate classification results than the use of the proximity measure alone. This is because the density of a tissue may also have an impact on the proximity measure which however, may be more related to the type of the tissue from which a tumor stems than to the status of immune cell infiltration of the tumor.

The invention claimed is:

1. An image analysis method for tumor classification, the method comprising:
   receiving, by an image analysis system, at least one digital image of a tissue sample;
   analyzing, by the image analysis system, the at least one received image for identifying immune cells and tumor cells in the at least one received image;
   for each of the identified tumor cells, determining, by the image analysis system, a distance of said each identified tumor cell to a nearest immune cell;
   computing, by the image analysis system, a proximity measure as a function of the determined distance of said each identified tumor cell;
   in dependence on the proximity measure, classifying, by the image analysis system, the identified tumor cells into tumor cells of an inflammatory tumor or as tumor cells of a non-inflammatory tumor; and
   storing, by the image analysis system, the classifying on a storage medium and/or displaying the classifying on a display device,
   wherein the computation of the proximity measure as a function of the determined distances comprises
      identifying a first and a second sub-set of the identified tumor cells, the first sub-set selectively comprising tumor cells whose nearest immune cell is less than a predefined distance away, the second sub-set selectively comprising tumor cells whose nearest immune cell is at least the predefined distance away from the immune cell,
      computing a ratio of a number of tumor cells contained in the first sub-set and a number of tumor cells in the second sub-set, and
      using the ratio as the proximity measure, wherein higher the ratio, a higher the probability that the classification result indicates that the identified tumor cells belong to the inflammatory tumor.

2. The image analysis method of claim 1, the displaying of the classification result comprising:
   representing all identified tumor cells as first pixel blobs having a first color;
   representing all identified immune cells whose distance to its nearest tumor cells is below a threshold as second pixel blobs having a second color; and
   displaying the second pixel blobs as an overlay of the first pixel blobs.

3. The image analysis method of claim 1, the tissue sample being a whole slide tissue sample and the digital image being a whole slide image.

4. The image analysis method of claim 1, further comprising:
   analyzing the at least one received image for determining a tumor cell density of the identified tumor cells;
   wherein the classification of the identified tumor cells into tumor cells of the inflammatory tumor or as tumor cells of the non-inflammatory tumor comprises inputting the proximity measure and the tumor cell density into a classifier configured to perform the classification.

5. The image analysis method of claim 1, further comprising:
   analyzing the at least one received image for determining an immune cell density of the identified immune cells or of a particular type of immune cells;
   wherein the classification of the identified tumor cells into tumor cells of the inflammatory tumor or as tumor cells of the non-inflammatory tumor comprises inputting the proximity measure and the immune cell density into a classifier configured to perform the classification.

6. The image analysis method of claim 1, the identification of the tumor cells comprising:
   identifying proliferating non-lymphoid cells and using said identified proliferating non-lymphoid cells as the tumor cells; and/or
   identifying cells expressing a set of one or more tumor-specific biomarkers and using said identified cells as the tumor cells.

7. The image analysis method of claim 1,
   the identification of the immune cells comprising identifying cytotoxic T-cells and using the identified cytotoxic T-cells as the identified immune cells; and/or
   the identification of the immune cells comprising identifying T-helper-cells and using the identified T-helper-cells as the identified immune cells; and/or
   the identification of the immune cells comprising identifying macrophages and using the identified macrophages as the identified immune cells; and/or
   the identification of the immune cells comprising identifying memory cells and using the identified memory cells as the identified immune cells; and/or
   the identification of the immune cells comprising identifying B-cells and using the identified B-cells as the identified immune cells; and/or
   the identification of the immune cells comprising identifying activated T-cells and using the identified activated T cells as the identified immune cells; and/or
   the identification of the immune cells comprising identifying PD1+ immune cells and using the identified PD1+ immune cells as the identified immune cells, the identification of the tumor cells comprising identifying PDL1+ tumor cells and using the identified PDL1+ tumor cells as the identified tumor cells.

8. The image analysis method of claim 1,
   the identification of the immune cells comprising identifying regulatory T-cells and identifying immune cells of at least one type of immune cells that boosts an immune response; and selectively using the identified immune cells that boost the immune response but not the identified regulatory T-cells as the identified immune cells.

9. The image analysis method of claim 1, the predefined distance being an immunologically effective distance of the identified immune cells, the immunologically effective distance being a maximum distance within which the identified immune cell is able to directly or indirectly trigger the killing of or the performing of apoptosis by the tumor cell.

10. The image analysis method of claim 1, the predefined distance is in a range of 20 µm to 50 µm.

11. The image analysis method of claim 1, wherein in case the ratio exceeds a predefined percentage, e.g. 50%, the classification result indicates that the identified tumor cells belong to the inflammatory tumor.

12. The image analysis method of claim 1, the method further comprising:
   selectively in case the classification result indicates that the identified tumor cells belong to the inflammatory tumor, outputting a signal being indicative of a treatment recommendation to use a substance that boosts or modulates an immune response as a drug for treating the tumor.

13. The image analysis method of claim 1, the method further comprising:
   using the proximity measure in addition to or in replacement of an MSS-MSI status indicator for computing a prognosis of a responsiveness of the inflammatory tumor to a substance that boosts or modulates an immune response.

14. The image analysis method of claim 1, the identified tumor cells being colorectal cancer cells.

15. The image analysis method of claim 1, the identification of the immune cells comprising identifying immune cells of multiple different immune cell types by analyzing pixel intensity values in the at least one digital image representing a presence of different immune cell type specific biomarkers, and using the totality of the identified immune cells of the multiple different immune cell types as the identified immune cells for computing the proximity measure.

16. The image analysis method of claim 1, the tumor cells being identified as cells expressing at least a first tumor-type specific biomarker, the immune cells being identified as cells expressing at least a first immune cell type specific biomarker, the method further comprising:
   analyzing the at least one received image or a further image of the tissue sample for identifying further immune cells as cells expressing a second immune cell type specific biomarker;
   analyzing the at least one received image or the further image of the tissue sample for identifying further tumor cells as cells expressing a second tumor-type specific biomarker or using the identified immune cells as further tumor cells;
   for each of the identified further tumor cells, determining the distance of said further tumor cell to the nearest further immune cell;
   computing a further proximity measure as a function of said determined distances; and
   in dependence on the further proximity measure, sub-classifying the identified tumor cells and/or predicting the treatability of the tumor by a class of substances.

17. An image analysis method for tumor classification, the method comprising:
   receiving, by an image analysis system, at least one digital image of a tissue sample;
   analyzing, by the image analysis system, the at least one received image for identifying tumor cells in the at least one received image;
   analyzing, by the image analysis system, the identified tumor cells for identifying tumor regions, wherein a tumor region is a tissue region whose majority of cells consist of tumor cells;
   analyzing, by the image analysis system, the at least one received image for identifying immune cells lying within one of the identified tumor regions or lying within a boundary region around one of the tumor regions, the width of the boundary being smaller than 200 µm;
   for each of the identified immune cells, determining, by the image analysis system, a distance of said immune cell to the nearest tumor cell;
   computing, by the image analysis system, a proximity measure as a function of the determined distances;
   in dependence on the proximity measure, classifying, by the image analysis system, the identified tumor cells into tumor cells of an inflammatory tumor or as tumor cells of a non-inflammatory tumor; and
   storing, by the image analysis system, the classification result on a storage medium and/or displaying the classification result on a display device,
   wherein the computation of the proximity measure as a function of the determined distances comprises
      identifying a first and a second sub-set of the identified tumor cells, the first sub-set selectively comprising tumor cells whose nearest immune cell is less than a predefined distance away, the second sub-set selectively comprising tumor cells whose nearest immune cell is at least the predefined distance away from the immune cell,
      computing a ratio of a number of tumor cells contained in the first sub-set and a number of tumor cells in the second sub-set, and
   using the ratio as the proximity measure, wherein higher the ratio, a higher the probability that the classification result indicates that the identified tumor cells belong to the inflammatory tumor.

18. An image analysis method for tumor classification, the method comprising:
   receiving, by an image analysis system, at least one digital image of a tissue sample;
   analyzing, by the image analysis system, the at least one received image for identifying immune cells and tumor cells in the at least one received image;
   for each of the identified tumor cells, determining, by the image analysis system, a distance of said each identified tumor cell to a nearest immune cell;
   computing, by the image analysis system, a proximity measure as a function of the determined distance of said each identified tumor cell;
   in dependence on the proximity measure, classifying, by the image analysis system, the identified tumor cells into tumor cells of an inflammatory tumor or as tumor cells of a non-inflammatory tumor; and
   storing, by the image analysis system, the classifying on a storage medium and/or displaying the classifying on a display device
   wherein the computation of the proximity measure as a function of the determined distances comprises
      generating a histogram of the distances of the tumor cells to their respective nearest one of the identified immune cells, the histogram comprising at least two distance bins, the histogram covering a distance range of 0 µm to at least 50 µm, each of the bins corresponding to a bar of the histogram, each bar indicating a count of the identified tumor cells having a distance to their nearest immune cell that falls into said bin, connecting an upper end of a first bar with an upper end of a last bar with a line, the first bar corresponding to the one of the bins covering smallest distances of the distance range, the last bar corresponding to the one of the bins covering largest distances of the distance range, determining a slope of the line, and using the slope as the proximity measure, wherein in case the slope indicates that the tumor cell count of the first bar is higher than the tumor cell count of the last bar, the classification result is that the identified tumor cells belong to the inflammatory tumor.

19. An image analysis method for tumor classification, the method comprising:

receiving, by an image analysis system, a digital image of a tissue sample;

analyzing, by the image analysis system, the at least one received image for identifying tumor cells in the at least one received image;

analyzing, by the image analysis system, the identified tumor cells for identifying tumor regions, wherein a tumor region is a tissue region whose majority of cells consist of tumor cells;

analyzing, by the image analysis system, the at least one received image for identifying immune cells lying within one of the identified tumor regions or lying within a boundary region around one of the tumor regions, the width of the boundary being smaller than 200 µm;

for each of the identified immune cells, determining, by the image analysis system, a distance of said immune cell to the nearest tumor cell;

computing, by the image analysis system, a proximity measure as a function of the determined distances;

in dependence on the proximity measure, classifying, by the image analysis system, the identified tumor cells into tumor cells of an inflammatory tumor or as tumor cells of a non-inflammatory tumor; and storing, by the image analysis system, the classification result on a storage medium and/or displaying the classification result on a display device, wherein the computation of the proximity measure as a function of the determined distances comprises generating a histogram of the distances of the immune cells to their respective nearest one of the identified tumor cells, the histogram comprising at least two distance bins, the histogram covering a distance range of 0 µm to at least 50 µm, each of the bins corresponding to a bar of the histogram, each of the bars indicating a count of the identified immune cells having a distance to their nearest tumor cell that falls into said bin, connecting an upper end of a first one of the bars with the upper end of the last one of the bars with a line, the first bar corresponding to the one of the bins covering the smallest distances, the last bar corresponding to the one of the bins covering the largest distances of the distance range; determining the slope of the line, and using the slope as the proximity measure, wherein in case the slope indicates that the immune cell count of the first bar is higher than the immune cell count of the last bar, the classification result is that the identified tumor cells belong to an inflammatory tumor.

20. An image analysis system for tumor classification, the system being configured for:

receiving at least one digital image of a tissue sample;

analyzing the at least one received image for identifying immune cells and tumor cells in the at least one received image;

for each of the identified tumor cells, determining a distance of said each identified tumor cell to a nearest immune cell;

computing a proximity measure as a function of the determined distance of said each identified tumor cell;

in dependence on the proximity measure, classifying the identified tumor cells into tumor cells of an inflammatory tumor or as tumor cells of a non-inflammatory tumor; and storing the classifying result on a storage medium and/or displaying the classifying result on a display device, wherein the computation of the proximity measure as a function of the determined distances comprises identifying a first and a second sub-set of the identified tumor cells, the first sub-set selectively comprising tumor cells whose nearest immune cell is less than a predefined distance away, the second sub-set selectively comprising tumor cells whose nearest immune cell is at least the predefined distance away from the immune cell, computing a ratio of a number of tumor cells contained in the first sub-set and a number of tumor cells in the second sub-set, and using the ratio as the proximity measure, wherein higher the ratio, a higher the probability that the classification result indicates that the identified tumor cells belong to the inflammatory tumor.

\* \* \* \* \*